US008440611B2

(12) United States Patent
Dong et al.

(10) Patent No.: US 8,440,611 B2
(45) Date of Patent: May 14, 2013

(54) ANALOGUES OF NEUROPEPTIDE Y HAVING AT LEAST ONE SYNTHETIC AMINO ACID SUBSTITUTION

(75) Inventors: Zheng Xin Dong, Holliston, MA (US); Kevin Zhou, Mansfield, MA (US); Daniel B. Deoliveira, Bellingham, MA (US)

(73) Assignee: Ipsen Pharma S.A.S., Boulogne (FR)

( * ) Notice: Subject to any disclaimer, the term of this patent is extended or adjusted under 35 U.S.C. 154(b) by 0 days.

(21) Appl. No.: 13/202,030

(22) PCT Filed: Feb. 19, 2010

(86) PCT No.: PCT/US2010/000491
§ 371 (c)(1),
(2), (4) Date: Oct. 26, 2011

(87) PCT Pub. No.: WO2010/096186
PCT Pub. Date: Aug. 26, 2010

(65) Prior Publication Data
US 2012/0040885 A1     Feb. 16, 2012

Related U.S. Application Data

(60) Provisional application No. 61/208,151, filed on Feb. 20, 2009.

(51) Int. Cl.
*A61K 38/00* (2006.01)
(52) U.S. Cl.
USPC ............................................. 514/1.7; 514/1.1
(58) Field of Classification Search ................ 514/1, 1.7
See application file for complete search history.

(56) References Cited

U.S. PATENT DOCUMENTS

| | | | |
|---|---|---|---|
| 5,328,899 | A | 7/1994 | Boublik et al. |
| 2005/0019841 | A1 | 1/2005 | Garman et al. |
| 2006/0105942 | A1 | 5/2006 | Lewis et al. |
| 2006/0211610 | A1 | 9/2006 | Dong |
| 2007/0086942 | A1 | 4/2007 | Chang et al. |

FOREIGN PATENT DOCUMENTS

| | | |
|---|---|---|
| EP | 1208852 A1 | 5/2002 |
| WO | WO9500161 A1 | 1/1995 |

OTHER PUBLICATIONS

Söll, et al., Novel analogues of neuropeptide Y with a preference for the Y1-receptor, Eur. J. Biochem. 268:2828-2837, 2001.*
Dissertation ETH No. 13271, background information.*
Kasperkiewicz, et al., Current and prospective applications of non-proteinogenic amino acids in profi ling of proteases substrate specificity,Biol. Chem., vol. 393, pp. 843-851, 2012 (background).*
Tran, et al., Designing amino acid residues with single-conformations, Protein Engineering, Design & Selection, 19(9): 401-408, 2006 (background).*
Haack, M. et al., "Multiple Peptide Synthesis to Identify Bioactive Hormone Structures," 2007, Top Curr Chem, 278:243-288.
Wieland, H. A. et al., "Probing of the neuropeptide Y-$Y_1$ -receptors interaction with anti-receptor antibodies," 1998, Eur. J. Biochem., 255:595-603.
Balasubramaniam, A. et al., [D-TRP$^{32}$] Neuropeptide Y : A Competitive Antagonist of NPY in Rat Hypothalamus, 1994, J. Med. Chem., 37:811-815.
Ingenhoven, N. et al., "Molecular Characterization of the Human Neuropeptide Y $Y_2$-Receptor," 1999, Biochemistry, 38:6897-6902.
Langer, M. et al., "99mTc-Labeled Neuropeptide Y Analogues as Potential Tumor Imaging Agents," 2001, Am. Chem. Society, 12:1028-1034.
Baeza, C. R. et al., "Orthogonal Solid-Phase Synthesis of a Monobiotinylated Analog of Neuropeptide Y," 1992, Int'J. of Peptide & Protein Research, 39:195-200.
Hu, L. et al., "Neuropeptide Y Acylation Chemistry in Aqueous Solution: Significance to Synthesis of a Peptide-based Photoaffinity Label," 1994, J. of Protein Chemistry, 13:135-140.
Beck-Sickinger, A. G. et al., "Complete L-alanine scan of neuropeptide Y reveals ligands binding to $Y_1$ and $Y_2$ receptors with distinguished conformations," 1994, Eur. J. Biochem, 225:947-958.
Soll, R. M. et al., "Novel analogues of neuropeptide Y with a preference for the $Y_1$ -receptor," 2001, Eur. J. Biochem., 268:2828-2837.
Fuhlendorff, J. et al, [Leu31, Pro34]Neuropeptide Y: A Specific Y1 Receptor Agonist, Proceedings of the National Academy of Sciences of the USA, Jan. 1, 1990, p. 182-186, vol. 87, No. 1, Washington DC, US.

* cited by examiner

*Primary Examiner* — Karlheinz R Skowronek
*Assistant Examiner* — Khalid Kader
(74) *Attorney, Agent, or Firm* — Tony K. Uhm

(57) ABSTRACT

The present invention relates to novel analogues of neuropeptide Y, pharmaceutical compositions containing the same, pharmaceutical formulations containing the same, and method of treating diseases or conditions mediated by neuropeptide Y-receptor binding. More particularly, the present invention relates to novel analogues of neuropeptide Y having at least one unnatural amino acid substitution, such as 4Hyp at position 34 , that selectively bind to the neuropeptide Y1 receptor subtype compared to the neuropeptide Y2 receptor subtype.

23 Claims, No Drawings

SEQUENCE LISTING

<160> NUMBER OF SEQ ID NOS: 49

<210> SEQ ID NO 1
<211> LENGTH: 36
<212> TYPE: PRT
<213> ORGANISM: Homo sapiens
<220> FEATURE:
<221> NAME/KEY: MOD_RES
<222> LOCATION: (36)..(36)
<223> OTHER INFORMATION: AMIDATION

<400> SEQUENCE: 1

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 2
<211> LENGTH: 37
<212> TYPE: PRT
<213> ORGANISM: Artificial Sequence
<220> FEATURE:
<223> OTHER INFORMATION: Generic Formula
<220> FEATURE:
<221> NAME/KEY: MISC_FEATURE
<222> LOCATION: (1)..(1)
<223> OTHER INFORMATION: Xaa = Tyr, (X1,X2,X3,X4,X5)Phe, or
      HN-CH((CH2)n-N(R4R5))-C(O) where X1-5 where each of X1, X2, X3,
      X4, and X5 is, independently for each occurrence, H, F, Cl, Br, I,
      (C1-10)alkyl, substitute, n is 1-5, R4 and R5 are defined in USSN
      61/208153
<220> FEATURE:
<221> NAME/KEY: MISC_FEATURE
<222> LOCATION: (1)..(1)
<223> OTHER INFORMATION: HN-CH((CH2)n-N(R4R5))-C(O) such that R4 and R5
      each is, independently for each occurrence, H, (C1-40)alkyl,
      (C1-40)heteroalkyl, (C1-40)acyl, (C2-40)alkenyl, (C2-40)alkynyl,
      aryl(C1-40)alkyl, aryl(C1-40)acyl, substituted (C1-40)alkyl, or
<220> FEATURE:
<221> NAME/KEY: MISC_FEATURE
<222> LOCATION: (1)..(1)
<223> OTHER INFORMATION: HN-CH((CH2)n-N(R4R5))-C(O) such that R4 and R5
      each is, independently for each occurrence, substituted
      (C1-40)heteroalkyl, substituted (C1-40)acyl, substituted
      (C2-40)alkenyl, substituted (C2-40)alkynyl, or
<220> FEATURE:
<221> NAME/KEY: MISC_FEATURE
<222> LOCATION: (1)..(1)
<223> OTHER INFORMATION: HN-CH((CH2)n-N(R4R5))-C(O) such that R4 and R5
      each is, independently for each occurrence, substituted
      aryl(C1-40)acyl, (C1-40)alkylsulfonyl, or C(NH)-NH2, wherein when
      R4 is (C1-40)acyl, aryl(C1-40)acyl, substituted (C1-40)acyl, or
<220> FEATURE:
<221> NAME/KEY: MISC_FEATURE
<222> LOCATION: (1)..(1)
<223> OTHER INFORMATION: HN-CH((CH2)n-N(R4R5))-C(O) such that R4 and R5
      each is, independently for each occurrence,aryl(C1-40)acyl,
      substituted (C1-40)acyl, substituted aryl(C1-40)acyl,substituted
      aryl(C1-40)acyl,(C1-40)alkylsulfonyl, or
<220> FEATURE:
<221> NAME/KEY: MISC_FEATURE
<222> LOCATION: (1)..(1)
<223> OTHER INFORMATION: HN-CH((CH2)n-N(R4R5))-C(O) such that R4 and R5
      each is, independently for each occurrence, C(NH)-NH2, then R5 is
      H or (C1-C40)alkyl, (C1-40)heteroalkyl, (C2-40)alkenyl,
      (C2-40)alkynyl, aryl(C1-40)alkyl, or
<220> FEATURE:
<221> NAME/KEY: MISC_FEATURE
<222> LOCATION: (1)..(1)
<223> OTHER INFORMATION: HN-CH((CH2)n-N(R4R5))-C(O) such that R4 and R5
      each is, independently for each occurrence,substituted

```
        (C1-40)alkyl, substituted (C1-40)heteroalkyl, substituted
        (C2-40)alkenyl, substituted (C2-40)alkynyl, or substituted
        aryl(C1-40)alkyl
<220> FEATURE:
<221> NAME/KEY: MISC_FEATURE
<222> LOCATION: (1)..(1)
<220> FEATURE:
<221> NAME/KEY: MISC_FEATURE
<222> LOCATION: (1)..(1)
<223> OTHER INFORMATION: (R2R3)-Xaa such that R2 and R3 each is,
        independently for each occurrence, selected from the group
        consisting of substituted (C1-30)alkyl, substituted
        (C1-30)heteroalkyl, substituted (C2-30)acyl, substituted
        (C2-30)alkenyl, or
<220> FEATURE:
<221> NAME/KEY: MISC_FEATURE
<222> LOCATION: (1)..(1)
<223> OTHER INFORMATION: (R2R3)-Xaa such that R2 and R3 each is,
        independently for each occurrence, selected from the group
        consisting of substituted substituted (C2-30)alkynyl, substituted
        aryl(C1-30)alkyl, and substituted aryl(C1-30)acyl
<220> FEATURE:
<221> NAME/KEY: MISC_FEATURE
<222> LOCATION: (1)..(1)
<223> OTHER INFORMATION: (R2R3)-Xaa such that R2 and R3 each is,
        independently for each occurrence, selected from the group
        consisting of substituted substituted (C2-30)alkynyl, substituted
        aryl(C1-30)alkyl, and substituted aryl(C1-30)acyl; provided that
<220> FEATURE:
<221> NAME/KEY: MISC_FEATURE
<222> LOCATION: (1)..(1)
<223> OTHER INFORMATION: when R2 is (C1-30)acyl, aryl(C1-30)acyl,
        substituted (C2-30)acyl, or substituted aryl(C1-30)acyl, R3 is H,
        (C1-30)alkyl, (C1-30)heteroalkyl, (C2-30)alkenyl, (C2-30)alkynyl,
        or
<220> FEATURE:
<221> NAME/KEY: MISC_FEATURE
<222> LOCATION: (1)..(1)
<223> OTHER INFORMATION: when R2 is aryl(C1-30)alkyl, substituted
        (C1-30)alkyl, substituted (C1-30)heteroalkyl, substituted
        (C2-30)alkenyl, (C2-30)alkynyl, or substituted
        aryl(C1-30)alkyl
<220> FEATURE:
<221> NAME/KEY: MISC_FEATURE
<222> LOCATION: (2)..(2)
<223> OTHER INFORMATION: Xaa = Pro, trans-3-hydroxy-L-proline (3Hyp),
        cis-3-hydroxy-L-proline (cis-3Hyp), 4-hydroxyproline (4Hyp) or
        cis-4-hydroxy-L-proline (cis-4Hyp)
<220> FEATURE:
<221> NAME/KEY: MISC_FEATURE
<222> LOCATION: (3)..(3)
<223> OTHER INFORMATION: Xaa = Ser, alpha-aminobutyric acid (Abu),
        alpha-aminoisobutyric acid (Aib), Ala Thr or
        HN-CH((CH2)n-N(R4R5))-C(O) where n is 1-5, R4 and R5 are defined
        in USSN 61/208153
<220> FEATURE:
<221> NAME/KEY: MISC_FEATURE
<222> LOCATION: (3)..(4)
<223> OTHER INFORMATION: HN-CH((CH2)n-N(R4R5))-C(O) such that R4 and R5
        each is, independently for each occurrence, H, (C1-40)alkyl,
        (C1-40)heteroalkyl, (C1-40)acyl, (C2-40)alkenyl, (C2-40)alkynyl,
        aryl(C1-40)alkyl, aryl(C1-40)acyl, substituted (C1-40)alkyl, or
<220> FEATURE:
<221> NAME/KEY: MISC_FEATURE
<222> LOCATION: (3)..(4)
<223> OTHER INFORMATION: HN-CH((CH2)n-N(R4R5))-C(O) such that R4 and R5
        each is, independently for each occurrence, substituted
        (C1-40)heteroalkyl, substituted (C1-40)acyl, substituted
        (C2-40)alkenyl, substituted (C2-40)alkynyl, or
<220> FEATURE:
<221> NAME/KEY: MISC_FEATURE
<222> LOCATION: (3)..(4)
<223> OTHER INFORMATION: HN-CH((CH2)n-N(R4R5))-C(O) such that R4 and R5
        each is, independently for each occurrence,substituted
        aryl(C1-40)alkyl, substituted aryl(C1-40)acyl,
        (C1-40)alkylsulfonyl, or C(NH)-NH2, wherein when R4 is
<220> FEATURE:
<221> NAME/KEY: MISC_FEATURE
<222> LOCATION: (3)..(4)
<223> OTHER INFORMATION: HN-CH((CH2)n-N(R4R5))-C(O) such that R4 and R5
```

```
            each is, independently for each occurrence,aryl(C1-40)acyl,
            substituted (C1-40)acyl, substituted aryl(C1-40)acyl, substituted
            aryl(C1-40)acyl, (C1-40)alkylsulfonyl, or
<220> FEATURE:
<221> NAME/KEY: MISC_FEATURE
<222> LOCATION: (3)..(4)
<223> OTHER INFORMATION: HN-CH((CH2)n-N(R4R5))-C(O) such that R4 and R5
            each is, independently for each occurrence, C(NH)-NH2, then R5 is
            H or (C1-C40)alkyl, (C1-40)heteroalkyl, (C2-40)alkenyl,
            (C2-40)alkynyl, aryl(C1-40)alkyl, or
<220> FEATURE:
<221> NAME/KEY: MISC_FEATURE
<222> LOCATION: (3)..(4)
<223> OTHER INFORMATION: HN-CH((CH2)n-N(R4R5))-C(O) such that R4 and R5
            each is, independently for each occurrence, substituted
            (C1-40)alkyl, substituted (C1-40)heteroalkyl, substituted
            (C2-40)alkenyl, substituted (C2-40)alkynyl, or substituted
            aryl(C1-40)alkyl
<220> FEATURE:
<221> NAME/KEY: MISC_FEATURE
<222> LOCATION: (4)..(4)
<223> OTHER INFORMATION: Xaa = Lys, Arg, homoarginine (hArg),
            2,4-diaminobutyric acid (Dab), 2,3-diaminopropionic acid (Dap),
            ornithine (Orn) or HN-CH((CH2)n-N(R4R5))-C(O) where n is 1-5, R4
            and R5 are defined in USSN 61/208153
<220> FEATURE:
<221> NAME/KEY: MISC_FEATURE
<222> LOCATION: (5)..(6)
<223> OTHER INFORMATION: Xaa = Pro, trans-3-hydroxy-L-proline (3Hyp),
            cis-3-hydroxy-L-proline (cis-3Hyp), 4-hydroxyproline (4Hyp) or
            cis-4-hydroxy-L-proline (cis-4Hyp)
<220> FEATURE:
<221> NAME/KEY: MISC_FEATURE
<222> LOCATION: (6)..(7)
<223> OTHER INFORMATION: HN-CH((CH2)n-N(R4R5))-C(O) such that R4 and R5
            each is, independently for each occurrence, H, (C1-40)alkyl,
            (C1-40)heteroalkyl, (C1-40)acyl, (C2-40)alkenyl, (C2-40)alkynyl,
            aryl(C1-40)alkyl, aryl(C1-40)acyl, substituted (C1-40)alkyl, or
<220> FEATURE:
<221> NAME/KEY: MISC_FEATURE
<222> LOCATION: (6)..(7)
<223> OTHER INFORMATION: HN-CH((CH2)n-N(R4R5))-C(O) such that R4 and R5
            each is, independently for each occurrence, substituted
            (C1-40)heteroalkyl, substituted (C1-40)acyl, substituted
            (C2-40)alkenyl, substituted (C2-40)alkynyl, or
<220> FEATURE:
<221> NAME/KEY: MISC_FEATURE
<222> LOCATION: (6)..(7)
<223> OTHER INFORMATION: HN-CH((CH2)n-N(R4R5))-C(O) such that R4 and R5
            each is, independently for each occurrence,substituted
            aryl(C1-40)alkyl, substituted aryl(C1-40)acyl,
            (C1-40)alkylsulfonyl, or C(NH)-NH2, wherein when R4 is
<220> FEATURE:
<221> NAME/KEY: MISC_FEATURE
<222> LOCATION: (6)..(7)
<223> OTHER INFORMATION: HN-CH((CH2)n-N(R4R5))-C(O) such that R4 and R5
            each is, independently for each occurrence, aryl(C1-40)acyl,
            substituted (C1-40)acyl, substituted aryl(C1-40)acyl, substituted
            aryl(C1-40)acyl, (C1-40)alkylsulfonyl, or
<220> FEATURE:
<221> NAME/KEY: MISC_FEATURE
<222> LOCATION: (6)..(7)
<223> OTHER INFORMATION: HN-CH((CH2)n-N(R4R5))-C(O) such that R4 and R5
            each is, independently for each occurrence, C(NH)-NH2, then R5 is
            H or (C1-C40)alkyl, (C1-40)heteroalkyl, (C2-40)alkenyl,
            (C2-40)alkynyl, aryl(C1-40)alkyl, or
<220> FEATURE:
<221> NAME/KEY: MISC_FEATURE
<222> LOCATION: (6)..(7)
<223> OTHER INFORMATION: HN-CH((CH2)n-N(R4R5))-C(O) such that R4 and R5
            each is, independently for each occurrence, substituted
            (C1-40)alkyl, substituted (C1-40)heteroalkyl, substituted
            (C2-40)alkenyl, substituted (C2-40)alkynyl, or substituted
            aryl(C1-40)alkyl
<220> FEATURE:
<221> NAME/KEY: MISC_FEATURE
<222> LOCATION: (7)..(7)
<223> OTHER INFORMATION: Xaa = Asn, alpha-aminoisobutyric acid (Aib),
            Gln or HN-CH((CH2)n-N(R4R5))-C(O) where n is 1-5, R4 and R5 are
            defined in USSN 61/208153
```

```
<220> FEATURE:
<221> NAME/KEY: MISC_FEATURE
<222> LOCATION: (8)..(8)
<223> OTHER INFORMATION: Xaa = Pro, trans-3-hydroxy-L-proline (3Hyp),
      cis-3-hydroxy-L-proline (cis-3Hyp), 4-hydroxyproline (4Hyp) or
      cis-4-hydroxy-L-proline (cis-4Hyp)
<220> FEATURE:
<221> NAME/KEY: MISC_FEATURE
<222> LOCATION: (9)..(9)
<223> OTHER INFORMATION: Xaa = Gly, alpha-aminoisobutyric acid (Aib) or
      HN-CH((CH2)n-N(R4R5))-C(O) where n is 1-5, R4 and R5 are defined
      in USSN 61/208153
<220> FEATURE:
<221> NAME/KEY: MISC_FEATURE
<222> LOCATION: (9)..(12)
<223> OTHER INFORMATION: HN-CH((CH2)n-N(R4R5))-C(O) such that R4 and R5
      each is, independently for each occurrence, H, (C1-40)alkyl,
      (C1-40)heteroalkyl, (C1-40)acyl, (C2-40)alkenyl, (C2-40)alkynyl,
      aryl(C1-40)alkyl, aryl(C1-40)acyl, substituted (C1-40)alkyl, or
<220> FEATURE:
<221> NAME/KEY: MISC_FEATURE
<222> LOCATION: (9)..(12)
<223> OTHER INFORMATION: HN-CH((CH2)n-N(R4R5))-C(O) such that R4 and R5
      each is, independently for each occurrence, substituted
      (C1-40)heteroalkyl, substituted (C1-40)acyl, substituted
      (C2-40)alkenyl, substituted (C2-40)alkynyl, or
<220> FEATURE:
<221> NAME/KEY: MISC_FEATURE
<222> LOCATION: (9)..(12)
<223> OTHER INFORMATION: HN-CH((CH2)n-N(R4R5))-C(O) such that R4 and R5
      each is, independently for each occurrence, substituted
      aryl(C1-40)alkyl, substituted aryl(C1-40)acyl,
      (C1-40)alkylsulfonyl, or C(NH)-NH2, wherein when R4 is
<220> FEATURE:
<221> NAME/KEY: MISC_FEATURE
<222> LOCATION: (9)..(12)
<223> OTHER INFORMATION: HN-CH((CH2)n-N(R4R5))-C(O) such that R4 and R5
      each is, independently for each occurrence, aryl(C1-40)acyl,
      substituted (C1-40)acyl, substituted aryl(C1-40)acyl, substituted
      aryl(C1-40)acyl, (C1-40)alkylsulfonyl, or
<220> FEATURE:
<221> NAME/KEY: MISC_FEATURE
<222> LOCATION: (9)..(12)
<223> OTHER INFORMATION: HN-CH((CH2)n-N(R4R5))-C(O) such that R4 and R5
      each is, independently for each occurrence, C(NH)-NH2, then R5 is
      H or (C1-C40)alkyl, (C1-40)heteroalkyl, (C2-40)alkenyl,
      (C2-40)alkynyl, aryl(C1-40)alkyl, or
<220> FEATURE:
<221> NAME/KEY: MISC_FEATURE
<222> LOCATION: (9)..(12)
<223> OTHER INFORMATION: HN-CH((CH2)n-N(R4R5))-C(O) such that R4 and R5
      each is, independently for each occurrence,substituted
      (C1-40)alkyl, substituted (C1-40)heteroalkyl, substituted
      (C2-40)alkenyl, substituted (C2-40)alkynyl, or substituted
      aryl(C1-40)alkyl
<220> FEATURE:
<221> NAME/KEY: MISC_FEATURE
<222> LOCATION: (10)..(10)
<223> OTHER INFORMATION: Xaa = Glu, alpha-aminoisobutyric acid (Aib),
      Asn, Asp, Gln or HN-CH((CH2)n-N(R4R5))-C(O) where n is 1-5, R4 and
      R5 are defined in USSN 61/208153
<220> FEATURE:
<221> NAME/KEY: MISC_FEATURE
<222> LOCATION: (11)..(11)
<223> OTHER INFORMATION: Xaa = Asp, alpha-aminoisobutyric acid (Aib),
      Asn, Gln, Glu or HN-CH((CH2)n-N(R4R5))-C(O) where n is 1-5, R4 and
      R5 are defined in USSN 61/208153
<220> FEATURE:
<221> NAME/KEY: MISC_FEATURE
<222> LOCATION: (12)..(12)
<223> OTHER INFORMATION: Xaa = Ala, alpha-aminobutyric acid (Abu),
      alpha-aminoisobutyric acid (Aib), norvaline (Nva), Val or
      HN-CH((CH2)n-N(R4R5))-C(O) where n is 1-5, R4 and R5 are defined
      in USSN 61/208153
<220> FEATURE:
<221> NAME/KEY: MISC_FEATURE
<222> LOCATION: (13)..(13)
<223> OTHER INFORMATION: Xaa = Pro, trans-3-hydroxy-L-proline (3Hyp),
      cis-3-hydroxy-L-proline (cis-3Hyp), 4-hydroxyproline (4Hyp) or
      cis-4-hydroxy-L-proline (cis-4Hyp)
```

```
<220> FEATURE:
<221> NAME/KEY: MISC_FEATURE
<222> LOCATION: (14)..(14)
<223> OTHER INFORMATION: Xaa = Ala, alpha-aminobutyric acid (Abu),
      alpha-aminoisobutyric acid (Aib), norvaline (Nva), Val or
      HN-CH((CH2)n-N(R4R5))-C(O) where n is 1-5, R4 and R5 are defined
      in USSN 61/208153
<220> FEATURE:
<221> NAME/KEY: MISC_FEATURE
<222> LOCATION: (14)..(37)
<223> OTHER INFORMATION: HN-CH((CH2)n-N(R4R5))-C(O) such that R4 and R5
      each is, independently for each occurrence, H, (C1-40)alkyl,
      (C1-40)heteroalkyl, (C1-40)acyl, (C2-40)alkenyl, (C2-40)alkynyl,
      aryl(C1-40)alkyl, aryl(C1-40)acyl, substituted (C1-40)alkyl, or
<220> FEATURE:
<221> NAME/KEY: MISC_FEATURE
<222> LOCATION: (14)..(37)
<223> OTHER INFORMATION: HN-CH((CH2)n-N(R4R5))-C(O) such that R4 and R5
      each is, independently for each occurrence, substituted
      (C1-40)heteroalkyl, substituted (C1-40)acyl, substituted
      (C2-40)alkenyl, substituted (C2-40)alkynyl, or
<220> FEATURE:
<221> NAME/KEY: MISC_FEATURE
<222> LOCATION: (14)..(37)
<223> OTHER INFORMATION: HN-CH((CH2)n-N(R4R5))-C(O) such that R4 and R5
      each is, independently for each occurrence, substituted
      aryl(C1-40)alkyl, substituted aryl(C1-40)acyl,
      (C1-40)alkylsulfonyl, or C(NH)-NH2, wherein when R4 is
<220> FEATURE:
<221> NAME/KEY: MISC_FEATURE
<222> LOCATION: (14)..(37)
<223> OTHER INFORMATION: HN-CH((CH2)n-N(R4R5))-C(O) such that R4 and R5
      each is, independently for each occurrence, aryl(C1-40)acyl,
      substituted (C1-40)acyl, substituted aryl(C1-40)acyl, substituted
      aryl(C1-40)acyl, (C1-40)alkylsulfonyl, or
<220> FEATURE:
<221> NAME/KEY: MISC_FEATURE
<222> LOCATION: (14)..(37)
<223> OTHER INFORMATION: HN-CH((CH2)n-N(R4R5))-C(O) such that R4 and R5
      each is, independently for each occurrence, C(NH)-NH2, then R5 is
      H or (C1-C40)alkyl, (C1-40)heteroalkyl, (C2-40)alkenyl,
      (C2-40)alkynyl, aryl(C1-40)alkyl, or
<220> FEATURE:
<221> NAME/KEY: MISC_FEATURE
<222> LOCATION: (14)..(37)
<223> OTHER INFORMATION: HN-CH((CH2)n-N(R4R5))-C(O) such that R4 and R5
      each is, independently for each occurrence, substituted
      (C1-40)alkyl, substituted (C1-40)heteroalkyl, substituted
      (C2-40)alkenyl, substituted (C2-40)alkynyl, or substituted
      aryl(C1-40)alkyl
<220> FEATURE:
<221> NAME/KEY: MISC_FEATURE
<222> LOCATION: (15)..(15)
<223> OTHER INFORMATION: Xaa = Glu, alpha-aminoisobutyric acid (Aib),
      Asn, Asp, Gln or HN-CH((CH2)n-N(R4R5))-C(O) where n is 1-5, R4 and
      R5 are defined in USSN 61/208153
<220> FEATURE:
<221> NAME/KEY: MISC_FEATURE
<222> LOCATION: (16)..(16)
<223> OTHER INFORMATION: Xaa = Asp, alpha-aminoisobutyric acid (Aib),
      Asn, Gln, Glu or HN-CH((CH2)n-N(R4R5))-C(O) where n is 1-5, R4 and
      R5 are defined in USSN 61/208153
<220> FEATURE:
<221> NAME/KEY: MISC_FEATURE
<222> LOCATION: (17)..(17)
<223> OTHER INFORMATION: Xaa = Met, 1-amino-1-cyclo(C3-9)alkyl
      carboxylic acid (Acc), alpha-aminoisobutyric acid (Aib),
      beta-cyclohexylalanine (Cha), Ile, Leu, homo-, nor-, tert-leucine
      (hLeu, Nle,Tle), norvaline (Nva), Val or
<220> FEATURE:
<221> NAME/KEY: MISC_FEATURE
<222> LOCATION: (17)..(17)
<223> OTHER INFORMATION: Xaa = HN-CH((CH2)n-N(R4R5))-C(O) where n is
      1-5, R4 and R5 are defined in USSN 61/208153
<220> FEATURE:
<221> NAME/KEY: MISC_FEATURE
<222> LOCATION: (18)..(18)
<223> OTHER INFORMATION: Xaa = Ala, alpha-aminobutyric acid (Abu),
      alpha-aminoisobutyric acid (Aib), norvaline (Nva), Val or
      HN-CH((CH2)n-N(R4R5))-C(O) where n is 1-5, R4 and R5 are defined
```

-continued

```
        in USSN 61/208153
<220> FEATURE:
<221> NAME/KEY: MISC_FEATURE
<222> LOCATION: (19)..(19)
<223> OTHER INFORMATION: Xaa = Arg, homoarginine (hArg),
      4-amino-4-carboxypiperidine (Apc), 2,4-diaminobutyric acid (Dab),
      2,3-diaminopropionic acid (Dap), Lys, ornithine (Orn) or
      HN-CH((CH2)n-N(R4R5))-C(O) where n is 1-5, R4 and R5 are defined
      in USSN 61/208153
<220> FEATURE:
<221> NAME/KEY: MISC_FEATURE
<222> LOCATION: (20)..(21)
<223> OTHER INFORMATION: Xaa = Tyr, (X1,X2,X3,X4,X5)Phe, or
      HN-CH((CH2)n-N(R4R5))-C(O) where X1-5, n is 1-5, R4 and R5 are
      defined in USSN 61/208153
<220> FEATURE:
<221> NAME/KEY: MISC_FEATURE
<222> LOCATION: (22)..(22)
<223> OTHER INFORMATION: Xaa = Ser, alpha-aminobutyric acid (Abu),
      alpha-aminoisobutyric acid (Aib), Ala, Thr or
      HN-CH((CH2)n-N(R4R5))-C(O) where n is 1-5, R4 and R5 are defined
      in USSN 61/208153
<220> FEATURE:
<221> NAME/KEY: MISC_FEATURE
<222> LOCATION: (23)..(23)
<223> OTHER INFORMATION: Xaa = Ala, alpha-aminobutyric acid (Abu),
      alpha-aminoisobutyric acid (Aib), norvaline (Nva), Val or
      HN-CH((CH2)n-N(R4R5))-C(O) where n is 1-5, R4 and R5 are defined
      in USSN 61/208153
<220> FEATURE:
<221> NAME/KEY: MISC_FEATURE
<222> LOCATION: (24)..(24)
<223> OTHER INFORMATION: Xaa = Leu, 1-amino-1-cyclo(C3-9)alkyl
      carboxylic acid (Acc), beta-cyclohexylalanine (Cha), Ile,
      homoleucine (hLeu), norleucine Nle), norvaline (Nva), tert-leucine
      (Tle), Val or
<220> FEATURE:
<221> NAME/KEY: MISC_FEATURE
<222> LOCATION: (24)..(24)
<223> OTHER INFORMATION: Xaa = HN-CH((CH2)n-N(R4R5))-C(O) where n is
      1-5, R4 and R5 are defined in USSN 61/208153
<220> FEATURE:
<221> NAME/KEY: MISC_FEATURE
<222> LOCATION: (25)..(25)
<223> OTHER INFORMATION: Xaa = Arg, homoarginine (hArg),
      4-amino-4-carboxypiperidine (Apc), 2,4-diaminobutyric acid (Dab),
      2,3-diaminopropionic acid (Dap), Lys, ornithine (Orn) or
      HN-CH((CH2)n-N(R4R5))-C(O) where n is 1-5, R4 and R5 are defined
      in USSN 61/208153
<220> FEATURE:
<221> NAME/KEY: MISC_FEATURE
<222> LOCATION: (26)..(26)
<223> OTHER INFORMATION: Xaa = His, beta-(2-pyridyl)alanine (2Pal),
      beta-(3-pyridyl)alanine (3Pal), beta-(4-pyridyl)alanine (4Pal) or
      HN-CH((CH2)n-N(R4R5))-C(O) where n is 1-5, R4 and R5 are defined
      in USSN 61/208153
<220> FEATURE:
<221> NAME/KEY: MISC_FEATURE
<222> LOCATION: (27)..(27)
<223> OTHER INFORMATION: Xaa = Tyr, (X1,X2,X3,X4,X5)Phe, or
      HN-CH((CH2)n-N(R4R5))-C(O) where X1-5, n is 1-5, R4 and R5 are
      defined in USSN 61/208153
<220> FEATURE:
<221> NAME/KEY: MISC_FEATURE
<222> LOCATION: (28)..(28)
<223> OTHER INFORMATION: Xaa = Ile, 1-amino-1-cyclo(C3-9)alkyl
      carboxylic acid (Acc), beta-cyclohexylalanine (Cha), Leu,
      homoleucine (hLeu), norleucine (Nle), norvaline (Nva), tertleucine
      (Tle), Val or
<220> FEATURE:
<221> NAME/KEY: MISC_FEATURE
<222> LOCATION: (28)..(28)
<223> OTHER INFORMATION: Xaa = HN-CH((CH2)n-N(R4R5))-C(O) where n is
      1-5, R4 and R5 are defined in USSN 61/208153
<220> FEATURE:
<221> NAME/KEY: MISC_FEATURE
<222> LOCATION: (29)..(29)
<223> OTHER INFORMATION: Xaa = Asn, alpha-aminoisobutyric acid (Aib),
      Gln or HN-CH((CH2)n-N(R4R5))-C(O) where n is 1-5, R4 and R5 are
      defined in USSN 61/208153
```

```
<220> FEATURE:
<221> NAME/KEY: MISC_FEATURE
<222> LOCATION: (30)..(30)
<223> OTHER INFORMATION: Xaa = Leu, 1-amino-1-cyclo(C3-9)alkyl
      carboxylic acid (Acc), beta-cyclohexylalanine (Cha), Ile,
      homoleucine (hLeu), norleucine (Nle), norvaline (Nva),
      tert-leucine (Tle), Val or
<220> FEATURE:
<221> NAME/KEY: MISC_FEATURE
<222> LOCATION: (30)..(30)
<223> OTHER INFORMATION: Xaa = HN-CH((CH2)n-N(R4R5))-C(O) where n is
      1-5, R4 and R5 are defined in USSN 61/20815
<220> FEATURE:
<221> NAME/KEY: MISC_FEATURE
<222> LOCATION: (31)..(31)
<223> OTHER INFORMATION: Xaa = HN-CH((CH2)n-N(R4R5))-C(O) where n is
      1-5 R4 and R5 are defined in USSN 61/20815
<220> FEATURE:
<221> NAME/KEY: MISC_FEATURE
<222> LOCATION: (31)..(31)
<223> OTHER INFORMATION: Xaa = Ile, 1-amino-1-cyclo(C3-9)alkyl
      carboxylic acid (Acc), beta-cyclohexylalanine (Cha), Leu,
      homoleucine (hLeu), norleucine (Nle), norvaline (Nva), tertleucine
      (Tle), Val or
<220> FEATURE:
<221> NAME/KEY: MISC_FEATURE
<222> LOCATION: (32)..(32)
<223> OTHER INFORMATION: Xaa = Thr, alpha-aminoisobutyric acid (Aib),
      Ser or HN-CH((CH2)n-N(R4R5))-C(O) where n is 1-5, R4 and R5 are
      defined in USSN 61/208153
<220> FEATURE:
<221> NAME/KEY: MISC_FEATURE
<222> LOCATION: (33)..(33)
<223> OTHER INFORMATION: Xaa = Arg, homoarginine (hArg),
      4-amino-4-carboxypiperidine (Apc), 2,4-diaminobutyric acid (Dab),
      2,3-diaminopropionic acid (Dap), Lys, ornithine (Orn) or
      HN-CH((CH2)n-N(R4R5))-C(O) where n is 1-5, R4 and R5 are defined
      in USSN 61/208153
<220> FEATURE:
<221> NAME/KEY: MISC_FEATURE
<222> LOCATION: (34)..(34)
<223> OTHER INFORMATION: Xaa = Gln, Asn, 3,4-dehydroproline (Dhp),
      trans-3-hydroxy-L-proline (3Hyp), cis-3-hydroxy-L-proline
      (cis-3Hyp), 4-hydroxyproline (4Hyp), cis-4-hydroxy-L-proline
      (cis-4Hyp), isonipecotic acid (Inp), or
<220> FEATURE:
<221> NAME/KEY: MISC_FEATURE
<222> LOCATION: (34)..(34)
<223> OTHER INFORMATION: Xaa = 4-ketoproline (Ktp), nipecotic acid
      (Nip), octahydroindole-2-carboxylic acid (Oic), Pro, homoproline
      (hPro), 1,2,3,4-tetrahydroisoquinoline-3-carboxylic acid (Tic) or
      HN-CH((CH2)0-5-N(R2R3))-C(O) where
<220> FEATURE:
<221> NAME/KEY: MISC_FEATURE
<222> LOCATION: (34)..(34)
<223> OTHER INFORMATION: Xaa = where each of R2 and R3 is, independently
      for each occurrence, H, (C1-40)alkyl, (C1-40)heteroalkyl,
      (C1-40)acyl, (C2-40)alkenyl, or
<220> FEATURE:
<221> NAME/KEY: MISC_FEATURE
<222> LOCATION: (34)..(34)
<223> OTHER INFORMATION: Xaa = where each of R2 and R3 is, independently
      for each occurrence, (C2-40)alkynyl, aryl(C1-40)alkyl,
      aryl(C1-40)acyl, substituted (C1-40)alkyl, substituted
      (C1-40)heteroalkyl, substituted (C1-40)acyl, or
<220> FEATURE:
<221> NAME/KEY: MISC_FEATURE
<222> LOCATION: (34)..(34)
<223> OTHER INFORMATION: Xaa = where each of R2 and R3 is, independently
      for each occurrence, substituted (C2-40)alkenyl, substituted
      (C2-40)alkynyl, substituted aryl(C1-40)alkyl, substituted
      aryl(C1-40)acyl, or
<220> FEATURE:
<221> NAME/KEY: MISC_FEATURE
<222> LOCATION: (34)..(34)
<223> OTHER INFORMATION: Xaa = where each of R2 and R3 is, independently
      for each occurrence, (C1-40)alkylsulfonyl, or C(NH)-NH2, wherein
      when R2 is (C1-40)acyl, aryl(C1-40)acyl, substituted (C1-40)acyl,
      or
<220> FEATURE:
```

```
<221> NAME/KEY: MISC_FEATURE
<222> LOCATION: (34)..(34)
<223> OTHER INFORMATION: Xaa = wherein when R2 is substituted
      aryl(C1-40)acyl, (C1-40)alkylsulfonyl, or C(NH)-NH2, then R3 is H
      or (C1-C40)alkyl, (C1-40)heteroalkyl, (C2-40)alkenyl,
<220> FEATURE:
<221> NAME/KEY: MISC_FEATURE
<222> LOCATION: (34)..(34)
<223> OTHER INFORMATION: Xaa = then R3 is (C2-40)alkynyl,
      aryl(C1-40)alkyl, substituted (C1-40)alkyl, substituted
      (C1-40)heteroalkyl, substituted (C2-40)alkenyl, substituted
      (C2-40)alkynyl, or substituted aryl(C1-40)alkyl.
<220> FEATURE:
<221> NAME/KEY: MISC_FEATURE
<222> LOCATION: (35)..(35)
<223> OTHER INFORMATION: Xaa = Arg, Aic, Apc, hArg, Dab, Dap, Lys, Orn,
      NH2Phe, NH2CH2Phe, or HN-CH((CH2)n-N(R4R5))-C(O) where n is 1-5,
      R4 and R5 are defined in USSN 61/208153
<220> FEATURE:
<221> NAME/KEY: MISC_FEATURE
<222> LOCATION: (35)..(36)
<223> OTHER INFORMATION: Xaa = Tyr, Aic, (X1,X2,X3,X4,X5)Phe, or
      HN-CH((CH2)n-N(R4R5))-C(O) where n is 1-5, R4 and R5 are defined
      in USSN 61/208153
<220> FEATURE:
<221> NAME/KEY: MISC_FEATURE
<222> LOCATION: (37)..(37)
<223> OTHER INFORMATION: Xaa = Deleted or HN-CH((CH2)n-N(R4R5))-C(O)
      where n is 1-5, R4 and R5 are defined in USSN 61/208153
<220> FEATURE:
<221> NAME/KEY: MISC_FEATURE
<222> LOCATION: (37)..(37)
<223> OTHER INFORMATION: Xaa-R1 such that R1 is OH, NH2, (C1-30)alkoxy,
      or NH-X6-CH2-X7, wherein X6 is a (C1-40)alkyl or (C2-40)alkenyl,
      and wherein X7 is H, OH, CO2H, or C(O)-NH2

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa
        35

<210> SEQ ID NO 3
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 3

Tyr Pro Ser Lys Pro Asp Asn Pro Gly Xaa Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 4
```

```
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 4

Tyr Pro Ser Lys Pro Asp Asn Pro Gly Glu Asp Ala Pro Ala Glu Asp
1               5                   10                  15

Xaa Ala Arg Tyr Tyr Ser Ala Leu Arg His Tyr Ile Asn Leu Ile Thr
                20                  25                  30

Arg Xaa Arg Tyr
        35

<210> SEQ ID NO 5
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 5

Tyr Pro Ser Lys Pro Asp Asn Pro Gly Glu Xaa Ala Pro Ala Glu Asp
1               5                   10                  15

Xaa Ala Arg Tyr Tyr Ser Ala Leu Arg His Tyr Ile Asn Leu Ile Thr
                20                  25                  30

Arg Xaa Arg Tyr
        35

<210> SEQ ID NO 6
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION
```

```
<400> SEQUENCE: 6

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 7
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (22)..(22)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 7

Tyr Pro Ser Lys Pro Asp Asn Pro Gly Glu Asp Ala Pro Ala Glu Asp
1               5                   10                  15

Met Ala Arg Tyr Tyr Xaa Ala Leu Arg His Tyr Ile Asn Leu Ile Thr
            20                  25                  30

Arg Xaa Arg Tyr
        35

<210> SEQ ID NO 8
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (31)..(31)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 8

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Xaa Thr
            20                  25                  30

Arg Xaa Arg Tyr
        35

<210> SEQ ID NO 9
<211> LENGTH: 36
<212> TYPE: PRT
<213> ORGANISM: Artificial Sequence
<220> FEATURE:
```

-continued

<223> OTHER INFORMATION: synthetic analog of NPY
<220> FEATURE:
<221> NAME/KEY: MISC_FEATURE
<222> LOCATION: (30)..(30)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 9

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Xaa Ile Thr
            20                  25                  30

Arg Xaa Arg Tyr
        35

<210> SEQ ID NO 10
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (28)..(28)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 10

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Xaa Asn Leu Ile Thr
            20                  25                  30

Arg Xaa Arg Tyr
        35

<210> SEQ ID NO 11
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (3)..(3)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 11

```
Tyr Pro Xaa Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 12
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (24)..(24)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 12

Tyr Pro Ser Lys Pro Asp Asn Pro Gly Glu Asp Ala Pro Ala Glu Asp
1               5                   10                  15

Met Ala Arg Tyr Tyr Ser Ala Xaa Arg His Tyr Ile Asn Leu Ile Thr
            20                  25                  30

Arg Xaa Arg Tyr
        35

<210> SEQ ID NO 13
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (6)..(6)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 13

Tyr Pro Ser Lys Pro Xaa Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 14
<211> LENGTH: 36
<212> TYPE: PRT
<213> ORGANISM: Artificial Sequence
<220> FEATURE:
<223> OTHER INFORMATION: synthetic analog of NPY
<220> FEATURE:
```

```
<221> NAME/KEY: MISC_FEATURE
<222> LOCATION: (18)..(18)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 14

Tyr Pro Ser Lys Pro Asp Asn Pro Gly Glu Asp Ala Pro Ala Glu Asp
1               5                   10                  15

Met Xaa Arg Tyr Tyr Ser Ala Leu Arg His Tyr Ile Asn Leu Ile Thr
            20                  25                  30

Arg Xaa Arg Tyr
        35

<210> SEQ ID NO 15
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (29)..(29)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 15

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Xaa Leu Ile Thr
            20                  25                  30

Arg Xaa Arg Tyr
        35

<210> SEQ ID NO 16
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (32)..(32)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 16

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Xaa
```

```
                    20                  25                  30

Arg Xaa Arg Tyr
        35

<210> SEQ ID NO 17
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (23)..(23)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 17

Tyr Pro Ser Lys Pro Asp Asn Pro Gly Glu Asp Ala Pro Ala Glu Asp
1               5                   10                  15

Met Ala Arg Tyr Tyr Ser Xaa Leu Arg His Tyr Ile Asn Leu Ile Thr
                20                  25                  30

Arg Xaa Arg Tyr
        35

<210> SEQ ID NO 18
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (17)..(17)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 18

Tyr Pro Ser Lys Pro Asp Asn Pro Gly Glu Asp Ala Pro Ala Glu Asp
1               5                   10                  15

Xaa Ala Arg Tyr Tyr Ser Ala Leu Arg His Tyr Ile Asn Leu Ile Thr
                20                  25                  30

Arg Xaa Arg Tyr
        35

<210> SEQ ID NO 19
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
```

```
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 19

Tyr Pro Ser Lys Pro Asp Asn Pro Gly Glu Xaa Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 20
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (12)..(12)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 20

Tyr Pro Ser Lys Pro Asp Asn Pro Gly Glu Asp Xaa Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 21
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (14)..(14)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 21

Tyr Pro Ser Lys Pro Asp Asn Pro Gly Glu Asp Ala Pro Xaa Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35
```

<210> SEQ ID NO 22
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 22

Tyr Pro Ser Lys Pro Asp Asn Pro Gly Glu Asp Ala Pro Ala Xaa Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 23
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (16)..(16)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 23

Tyr Pro Ser Lys Pro Asp Asn Pro Gly Glu Asp Ala Pro Ala Glu Xaa
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 24
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (7)..(7)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES -continued

```
<222> LOCATION: (36)..(36)
<223> OTHER INFORMATION: AMIDATION

<400> SEQUENCE: 24

Tyr Pro Ser Lys Pro Asp Xaa Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 25
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (9)..(9)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 25

Tyr Pro Ser Lys Pro Asp Asn Pro Xaa Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 26
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 26

Tyr Pro Ser Lys Pro Asp Asn Pro Gly Xaa Asp Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35
```

```
<210> SEQ ID NO 27
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 27

Tyr Pro Ser Lys Pro Asp Asn Pro Gly Glu Asp Ala Pro Ala Xaa Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 28
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = norleucine (Nle)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 28

Tyr Pro Ser Lys Pro Asp Asn Pro Gly Glu Xaa Ala Pro Ala Xaa Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 29
<211> LENGTH: 36
<212> TYPE: PRT
<213> ORGANISM: Artificial Sequence
<220> FEATURE:
```

-continued

```
<223> OTHER INFORMATION: synthetic analog of NPY
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = norleucine (Nle)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 29

Tyr Pro Ser Lys Pro Asp Asn Pro Gly Xaa Asp Ala Pro Ala Xaa Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 30
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 30

Tyr Pro Ser Lys Pro Asp Asn Pro Gly Glu Xaa Ala Pro Ala Xaa Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 31
<211> LENGTH: 36
<212> TYPE: PRT
<213> ORGANISM: Artificial Sequence
<220> FEATURE:
<223> OTHER INFORMATION: synthetic analog of NPY
<220> FEATURE:
```

```
<221> NAME/KEY: MISC_FEATURE
<222> LOCATION: (12)..(12)
<223> OTHER INFORMATION: Xaa = alpha-aminoisobutyric acid (Aib)
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 31

Tyr Pro Ser Lys Pro Asp Asn Pro Gly Glu Asp Xaa Pro Ala Xaa Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 32
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (15)..(15)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 32

Tyr Pro Ser Lys Pro Asp Asn Pro Gly Xaa Asp Ala Pro Ala Xaa Asp
1               5                   10                  15

Xaa Ala Arg Tyr Tyr Ser Ala Leu Arg His Tyr Ile Asn Leu Ile Thr
            20                  25                  30

Arg Xaa Arg Tyr
        35

<210> SEQ ID NO 33
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (11)..(11)
```

```
<223> OTHER INFORMATION: Xaa = alpha-aminoisobutyric acid (Aib)
<220> FEATURE:
<221> NAME/KEY: MISC_FEATURE
<222> LOCATION: (16)..(16)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 33

Tyr Pro Ser Lys Pro Asp Asn Pro Gly Glu Xaa Ala Pro Ala Glu Xaa
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 34
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MISC_FEATURE
<222> LOCATION: (16)..(16)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MOD_RES
<222> LOCATION: (36)..(36)
<223> OTHER INFORMATION: AMIDATION

<400> SEQUENCE: 34

Tyr Pro Ser Lys Pro Asp Asn Pro Gly Xaa Asp Ala Pro Ala Glu Xaa
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 35
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
```

```
<221> NAME/KEY: MISC_FEATURE
<222> LOCATION: (35)..(36)
<223> OTHER INFORMATION: N-acetylated reduced peptide bond
<220> FEATURE:
<221> NAME/KEY: MOD_RES
<222> LOCATION: (36)..(36)
<223> OTHER INFORMATION: AMIDATION

<400> SEQUENCE: 35

Tyr Pro Ser Lys Pro Asp Asn Pro Gly Glu Xaa Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Lys Tyr
        35

<210> SEQ ID NO 36
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MISC_FEATURE
<222> LOCATION: (35)..(35)
<223> OTHER INFORMATION: Xaa = 4-amino-4-carboxypiperidine (Apc)
<220> FEATURE:
<221> NAME/KEY: MOD_RES
<222> LOCATION: (36)..(36)
<223> OTHER INFORMATION: AMIDATION

<400> SEQUENCE: 36

Tyr Pro Ser Lys Pro Asp Asn Pro Gly Glu Asp Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Xaa Tyr
        35

<210> SEQ ID NO 37
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MISC_FEATURE
<222> LOCATION: (36)..(36)
<223> OTHER INFORMATION: Xaa = 2-aminoindan-2-carboxylic acid (Aic)
<220> FEATURE:
<221> NAME/KEY: MOD_RES
<222> LOCATION: (36)..(36)
<223> OTHER INFORMATION: AMIDATION

<400> SEQUENCE: 37
```

```
Tyr Pro Ser Lys Pro Asp Asn Pro Gly Glu Asp Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Arg Xaa
        35
```

```
<210> SEQ ID NO 38
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MISC_FEATURE
<222> LOCATION: (35)..(35)
<223> OTHER INFORMATION: Xaa = 4NH2Phe
<220> FEATURE:
<221> NAME/KEY: MOD_RES
<222> LOCATION: (36)..(36)
<223> OTHER INFORMATION: AMIDATION

<400> SEQUENCE: 38

Tyr Pro Ser Lys Pro Asp Asn Pro Gly Glu Asp Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Xaa Tyr
        35
```

```
<210> SEQ ID NO 39
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MISC_FEATURE
<222> LOCATION: (35)..(35)
<223> OTHER INFORMATION: Xaa = 4NH2CH2Phe
<220> FEATURE:
<221> NAME/KEY: MOD_RES
<222> LOCATION: (36)..(36)
<223> OTHER INFORMATION: AMIDATION

<400> SEQUENCE: 39

Tyr Pro Ser Lys Pro Asp Asn Pro Gly Glu Asp Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Xaa Tyr
        35
```

```
<210> SEQ ID NO 40
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MISC_FEATURE
<222> LOCATION: (35)..(36)
<223> OTHER INFORMATION: reduced peptide bond
<220> FEATURE:
<221> NAME/KEY: MOD_RES
<222> LOCATION: (36)..(36)
<223> OTHER INFORMATION: AMIDATION

<400> SEQUENCE: 40

Tyr Pro Ser Lys Pro Asp Asn Pro Gly Glu Asp Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Lys Tyr
        35

<210> SEQ ID NO 41
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (17)..(17)
<223> OTHER INFORMATION: Xaa = alpha-aminoisobutyric acid (Aib)
<220> FEATURE:
<221> NAME/KEY: MISC_FEATURE
<222> LOCATION: (34)..(34)
<223> OTHER INFORMATION: Xaa = 4-hydroxyproline (4Hyp)
<220> FEATURE:
<221> NAME/KEY: MISC_FEATURE
<222> LOCATION: (35)..(36)
<223> OTHER INFORMATION: reduced peptide bond
<220> FEATURE:
<221> NAME/KEY: MOD_RES
<222> LOCATION: (36)..(36)
<223> OTHER INFORMATION: AMIDATION

<400> SEQUENCE: 41

Tyr Pro Ser Lys Pro Asp Asn Pro Gly Glu Xaa Ala Pro Ala Glu Asp
1               5                   10                  15

Xaa Ala Arg Tyr Tyr Ser Ala Leu Arg His Tyr Ile Asn Leu Ile Thr
            20                  25                  30

Arg Xaa Lys Tyr
        35

<210> SEQ ID NO 42
<211> LENGTH: 36
<212> TYPE: PRT
<213> ORGANISM: Artificial Sequence
<220> FEATURE:
<223> OTHER INFORMATION: synthetic analog of NPY
```

```
<220> FEATURE:
<221> NAME/KEY: MISC_FEATURE
<222> LOCATION: (34)..(34)
<223> OTHER INFORMATION: Xaa = nipecotic acid (Nip)
<220> FEATURE:
<221> NAME/KEY: MOD_RES
<222> LOCATION: (36)..(36)
<223> OTHER INFORMATION: AMIDATION

<400> SEQUENCE: 42

Tyr Pro Ser Lys Pro Asp Asn Pro Gly Glu Asp Ala Pro Ala Glu Asp
 1               5                  10                  15

Met Ala Arg Tyr Tyr Ser Ala Leu Arg His Tyr Ile Asn Leu Ile Thr
             20                  25                  30

Arg Xaa Arg Tyr
         35

<210> SEQ ID NO 43
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (34)..(34)
<223> OTHER INFORMATION: Xaa = isonipecotic acid (Inp)
<220> FEATURE:
<221> NAME/KEY: MOD_RES
<222> LOCATION: (36)..(36)
<223> OTHER INFORMATION: AMIDATION

<400> SEQUENCE: 43

Tyr Pro Ser Lys Pro Asp Asn Pro Gly Glu Asp Ala Pro Ala Glu Asp
 1               5                  10                  15

Met Ala Arg Tyr Tyr Ser Ala Leu Arg His Tyr Ile Asn Leu Ile Thr
             20                  25                  30

Arg Xaa Arg Tyr
         35

<210> SEQ ID NO 44
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (34)..(34)
<223> OTHER INFORMATION: Xaa = 3,4-dehydroproline (Dhp)
<220> FEATURE:
<221> NAME/KEY: MOD_RES
<222> LOCATION: (36)..(36)
<223> OTHER INFORMATION: AMIDATION

<400> SEQUENCE: 44

Tyr Pro Ser Lys Pro Asp Asn Pro Gly Glu Asp Ala Pro Ala Glu Asp
 1               5                  10                  15

Met Ala Arg Tyr Tyr Ser Ala Leu Arg His Tyr Ile Asn Leu Ile Thr
             20                  25                  30

Arg Xaa Arg Tyr
         35

<210> SEQ ID NO 45
<211> LENGTH: 36
<212> TYPE: PRT
<213> ORGANISM: Artificial Sequence
<220> FEATURE:
```

```
<223> OTHER INFORMATION: synthetic analog of NPY
<220> FEATURE:
<221> NAME/KEY: MISC_FEATURE
<222> LOCATION: (34)..(34)
<223> OTHER INFORMATION: Xaa = homoproline (hPro)
<220> FEATURE:
<221> NAME/KEY: MOD_RES
<222> LOCATION: (36)..(36)
<223> OTHER INFORMATION: AMIDATION

<400> SEQUENCE: 45

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 46
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MISC_FEATURE
<222> LOCATION: (34)..(34)
<223> OTHER INFORMATION: Xaa = 1,2,3,4-tetrahydroisoquinoline-3-
      carboxylic acid (Tic)
<220> FEATURE:
<221> NAME/KEY: MOD_RES
<222> LOCATION: (36)..(36)
<223> OTHER INFORMATION: AMIDATION

<400> SEQUENCE: 46

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Xaa Arg Tyr
        35

<210> SEQ ID NO 47
<211> LENGTH: 36
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (34)..(34)
<223> OTHER INFORMATION: C(O)-(CH2)12-CH3 coupled to the
      epsilon-nitrogen of the Lys sidechain
<220> FEATURE:
<221> NAME/KEY: MOD_RES
<222> LOCATION: (36)..(36)
<223> OTHER INFORMATION: AMIDATION

<400> SEQUENCE: 47

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Leu Thr
            20                  25                  30

Arg Lys Arg Tyr
        35

<210> SEQ ID NO 48
<211> LENGTH: 36
```

```
<212> TYPE: PRT
<213> ORGANISM: Artificial Sequence
<220> FEATURE:
<223> OTHER INFORMATION: synthetic analog of NPY
<220> FEATURE:
<221> NAME/KEY: MOD_RES
<222> LOCATION: (36)..(36)
<223> OTHER INFORMATION: AMIDATION

<400> SEQUENCE: 48

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Pro Arg Tyr
        35

<210> SEQ ID NO 49
<211> LENGTH: 36
<212> TYPE: PRT
<213> ORGANISM: Homo sapiens

<400> SEQUENCE: 49

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35
```

ANALOGUES OF NEUROPEPTIDE Y HAVING AT LEAST ONE SYNTHETIC AMINO ACID SUBSTITUTION

This application is a United States nation stage filing under 35 U.S.C. §371 of international (PCT) application no. PCT/US10/00491 filed Feb. 19 2010, designating the US, which claims priority to U.S. provisional application No. 61/208151 filed Feb. 20 2009.

FIELD OF THE INVENTION

The present invention relates to novel analogues of neuropeptide Y, pharmaceutical compositions containing the same, pharmaceutical formulations containing the same, and method of treating diseases or conditions mediated by neuropeptide Y-receptor binding. More particularly, the present invention relates to novel analogues of neuropeptide Y having at least one unnatural amino acid substitution, such as 4Hyp at position 34, that selectively bind to the neuropeptide Y1 receptor subtype compared to the neuropeptide Y2 receptor subtype.

BACKGROUND OF THE INVENTION

Neuropeptide Y ("NPY"), a 36 amino acid peptide neurotransmitter, is a member of the pancreatic family of peptides and shares significant sequence homology with pancreatic polypeptide and peptide YY. Human neuropeptide Y ("hNPY") has the sequence: H-Tyr-Pro-Ser-Lys-Pro-Asp-Asn-Pro-Gly-Glu-Asp-Ala-Pro-Ala-Glu-Asp-Met-Ala-Arg-Tyr-Tyr-Ser-Ala-Leu-Arg-His-Tyr-Ile-Asn-Leu-Ile-Thr-Arg-Gln-Arg-Tyr-NH$_2$ (SEQ ID NO:1). NPY was discovered, isolated and sequenced from porcine brain and was named "neuropeptide Y" due to its isolation from neural tissue and the presence of tyrosine as both the amino and carboxy terminal amino acid.

NPY and the other members of its family of peptides all feature a tertiary structure consisting of an N-terminal polyproline helix and an amphiphilic α-helix, connected with a β-turn, creating a hairpin-like loop, which is sometimes referred to as the "pancreatic polypeptide fold." The helices are kept together by hydrophobic interactions. The amidated C-terminal end projects away from the hairpin loop.

Subsequent to its discovery, NPY was identified as being the most abundant peptide in the central nervous system with widespread distribution including the cortex, brainstem, hippocampus, hypothalamus, amygdala, and thalamus, as well as being present in the peripheral nervous system in sympathetic neurons and adrenal chromaffin cells.

NPY seems to fulfill the main neurotransmitter criteria, since it is stored in synaptic granules, is released upon electrical nerve stimulation, and acts at specific receptors. It is clear that NPY is an important messenger in its own right, probably in the brain, where NPY potently inhibits the activity of adenylate cyclase and induces an increase in the intracellular levels of calcium. Central injection of NPY results in blood pressure changes, increased feeding, increased fat storage, elevated blood sugar and insulin, decreased locomotor activity, reduced body temperature, and catalepsy.

NPY appears to interact with a family of closely related receptors. These receptors are generally classified into several subtypes based upon the ability of different tissues and receptors to bind different fragments of neuropeptide Y and the closely related PYY. The Y1 receptor subtype ("NPY-Y1 receptor") appears to be the major vascular NPY receptor. The Y2 receptor subtype ("NPY-Y2 receptor") can also occur postjunctionally on vascular smooth muscle. The Y3 receptor subtype ("NPY-Y3 receptor") appears to be NPY-specific, not binding PYY. This receptor is likely to be present in the adrenal tissues, medulla, heart, and brain stem, among other areas. For a review of neuropeptide Y and neuropeptide Y receptors, see, e.g., C. Wahlestedt and D. Reis, Annual Review of Pharmacology and Toxicology, 33:309-352 (1993). Patent Cooperation Treaty ("PCT") Publication No. WO 95/00161 describes a series of NPY antagonists and agonists for controlling biological activities such as obesity and cardiovascular function.

European Pat. No. 0759441 and U.S. Pat. No. 5,576,337 report that physiological disorders related to an excess of neuropeptide Y include: disorders or diseases pertaining to the heart, blood vessels or the renal system, such as vasospasm, heart failure, shock, cardiac hypertrophy, increased blood pressure, angina, myocardial infarction, sudden cardiac death, arrhythmia, peripheral vascular disease, and abnormal renal conditions such as impaired flow of fluid, abnormal mass transport, or renal failure; conditions related to increased sympathetic nerve activity for example, during or after coronary artery surgery, and operations and surgery in the gastrointestinal tract; cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia; conditions related to pain or nociception; diseases related to abnormal gastrointestinal motility and secretion, such as different forms of ileus, urinary incontinence, and Crohn's disease; abnormal drink and food intake disorders, such as anorexia and metabolic disorders; diseases related to sexual dysfunction and reproductive disorders; conditions or disorders associated with inflammation; respiratory diseases, such as asthma and conditions related to asthma and bronchoconstriction; and diseases related to abnormal hormone release, such as leutinizing hormone, growth hormone, insulin, and prolactin.

PCT Publication No. WO 02/43776 by Reubi reports on the use of compounds that bind the NPY-Y1 receptor for the preparation of a pharmaceutical composition for the diagnosis or treatment of tumors expressing the NPY-Y1 receptor, in particular breast cancer, ovarian cancer and glioblastoma.

There are numerous patents and patent publications that disclose certain NPY analogues and uses thereof, such as U.S. Pat. Nos. 5,026,685, 5,328,899, 6,511,984, PCT Publication No. WO 02/43776, PCT Publication No. WO2007/039318, etc. Notwithstanding the foregoing, there remains a continuing need for NPY analogues having improved potency and/or selectivity and/or in vivo or in vitro characteristics.

SUMMARY OF THE INVENTION

In one aspect, the present invention provides peptide variants of hNPY of the following formula (I) (SEQ ID NO:2):

$$(R^2R^3)\text{-}A^1\text{-}A^2\text{-}A^3\text{-}A^4\text{-}A^5\text{-}A^6\text{-}A^7\text{-}A^8\text{-}A^9\text{-}A^{10}\text{-}A^{11}\text{-}A^{12}\text{-}$$
$$A^{13}\text{-}A^{14}\text{-}A^{15}\text{-}A^{16}\text{-}A^{17}\text{-}A^{18}\text{-}A^{19}\text{-}A^{20}\text{-}A^{21}\text{-}A^{22}\text{-}$$
$$A^{23}\text{-}A^{24}\text{-}A^{25}\text{-}A^{26}\text{-}A^{27}\text{-}A^{28}\text{-}A^{29}\text{-}A^{30}\text{-}A^{31}\text{-}A^{32}\text{-}$$
$$A^{33}\text{-}A^{34}\text{-}A^{35}\text{-}A^{36}\text{-}A^{37}\text{-}R^1 \quad (I)$$

wherein:

$A^1$ is Tyr, $(X^1, X^2, X^3, X^4, X^5)$Phe, or HN—CH$((CH_2)_n$—N$(R^4R^5))$—C(O);

$A^2$ is Pro, 3Hyp, cis-3Hyp, 4Hyp, or cis-4Hyp;

$A^3$ is Ser, Abu, Aib, Ala, Thr, or HN—CH$((CH_2)_n$—N$(R^4R^5))$—C(O);

$A^4$ is Lys, Arg, hArg, Dab, Dap, Orn, or HN—CH$((CH_2)_n$—N$(R^4R^5))$—C(O);

$A^5$ is Pro, 3Hyp, cis-3Hyp, 4Hyp, or cis-4Hyp;

$A^6$ is Asp, Aib, Asn, Gln, Glu, or HN—CH$((CH_2)_n$—N$(R^4R^5))$—C(O);

$A^7$ is Asn, Aib, Gln, or HN—CH$((CH_2)_n$—N$(R^4R^5))$—C(O);

$A^8$ is Pro, 3Hyp, cis-3Hyp, 4Hyp, or cis-4Hyp;

$A^9$ is Gly, Aib, or HN—CH$((CH_2)_n$—N$(R^4R^5))$—C(O);

$A^{10}$ is Glu, Aib, Asn, Asp, Gln, or HN—CH$((CH_2)_n$—N$(R^4R^5))$—C(O);

$A^{11}$ is Asp, Aib, Asn, Gln, Glu, or HN—CH$((CH_2)_n$—N$(R^4R^5))$—C(O);

$A^{12}$ is Ala, Abu, Aib, Nva, Val, or HN—CH$((CH_2)_n$—N$(R^4R^5))$—C(O);

$A^{13}$ is Pro, 3Hyp, cis-3Hyp, 4Hyp, or cis-4Hyp;

$A^{14}$ is Ala, Abu, Aib, Nva, Val, or HN—CH$((CH_2)_n$—N$(R^4R^5))$—C(O);

$A^{15}$ is Glu, Aib, Asn, Asp, Gln, or HN—CH$((CH_2)_n$—N$(R^4R^5))$—C(O);

$A^{16}$ is Asp, Aib, Asn, Gln, Glu, or HN—CH$((CH_2)_n$—N$(R^4R^5))$—C(O);

$A^{17}$ is Met, Acc, Aib, Cha, Ile, Leu, hLeu, Nle, Nva, Tle, Val, or HN—CH$((CH_2)_n$—N$(R^4R^5))$—C(O);

$A^{18}$ is Ala, Abu, Aib, Nva, Val, or HN—CH$((CH_2)_n$—N$(R^4R^5))$—C(O);

$A^{19}$ is Arg, hArg, Apc, Dab, Dap, Lys, Orn, or HN—CH$((CH_2)_n$—N$(R^4R^5))$—C(O);

$A^{20}$ is Tyr, $(X^1, X^2, X^3, X^4, X^5)$Phe, or HN—CH$((CH_2)_n$—N$(R^4R^5))$—C(O);

$A^{21}$ is Tyr, $(X^1, X^2, X^3, X^4, X^5)$Phe, or HN—CH$((CH_2)_n$—N$(R^4R^5))$—C(O);

$A^{22}$ is Ser, Abu, Aib, Ala, Thr, or HN—CH$((CH_2)_n$—N$(R^4R^5))$—C(O);

$A^{23}$ is Ala, Abu, Aib, Nva, Val, or HN—CH$((CH_2)_n$—N$(R^4R^5))$—C(O);

$A^{24}$ is Leu, Acc, Cha, Ile, hLeu, Nle, Nva, Tle, Val, or HN—CH$((CH_2)_n$—N$(R^4R^5))$—C(O);

$A^{25}$ is Arg, hArg, Dab, Dap, Lys, Orn, or HN—CH$((CH_2)_n$—N$(R^4R^5))$—C(O);

$A^{26}$ is His, 2 Pal, 3 Pal, 4 Pal, or HN—CH$((CH_2)_n$—N$(R^4R^5))$—C(O);

$A^{27}$ is Tyr, $(X^1, X^2, X^3, X^4, X^5)$Phe, or HN—CH$((CH_2)_n$—N$(R^4R^5))$—C(O);

$A^{28}$ is Ile, Acc, Cha, Leu, hLeu, Nle, Nva, Tle, Val, or HN—CH$((CH_2)_n$—N$(R^4R^5))$—C(O);

$A^{29}$ is Asn, Aib, Gln, or HN—CH$((CH_2)_n$—N$(R^4R^5))$—C(O);

$A^{30}$ is Leu, Acc, Cha, Ile, hLeu, Nle, Nva, Tle, Val, or HN—CH$((CH_2)_n$—N$(R^4R^5))$—C(O);

$A^{31}$ is Ile, Acc, Cha, Leu, hLeu, Nle, Nva, Tle, Val, or HN—CH$((CH_2)_n$—N$(R^4R^5))$—C(O);

$A^{32}$ is Thr, Aib, Ser, or HN—CH$((CH_2)_n$—N$(R^4R^5))$—C(O);

$A^{33}$ is Arg, hArg, Dab, Dap, Lys, Orn, or HN—CH$((CH_2)_n$—N$(R^4R^5))$—C(O);

$A^{34}$ is Gln, Asn, Dhp, 3Hyp, cis-3Hyp, 4Hyp, cis-4Hyp, Inp, Ktp, Nip, Oic, hPro, Tic, or HN—CH$((CH_2)_n$—N$(R^4R^5))$—C(O);

$A^{35}$ is Arg, Aic, Apc, hArg, Dab, Dap, Lys, Orn, NH$_2$Phe, NH$_2$CH$_2$Phe, or HN—CH$((CH_2)_n$—N$(R^4R^5))$—C(O);

$A^{36}$ is Tyr, Aic, $(X^1, X^2, X^3, X^4, X^5)$Phe, or HN—CH$((CH_2)_n$—N$(R^4R^5))$—C(O);

$A^{37}$ is HN—CH$((CH_2)_n$—N$(R^4R^5))$—C(O) or deleted;

$R^1$ is OH, NH$_2$, $(C_{1-30})$alkoxy, or NH—$X^6$—CH$_2$—$X^7$, wherein $X^6$ is a $(C_{1-40})$alkyl or $(C_{2-40})$alkenyl, and wherein $X^7$ is H, OH, CO$_2$H, or C(O)—NH$_2$;

$R^2$ and $R^3$ each is, independently for each occurrence, selected from the group consisting of H, $(C_{1-30})$alkyl, $(C_{1-30})$heteroalkyl, $(C_{1-30})$acyl, $(C_{2-30})$alkenyl, $(C_{2-30})$alkynyl, aryl$(C_{1-30})$alkyl, aryl$(C_{1-30})$acyl, substituted $(C_{1-30})$alkyl, substituted $(C_{1-30})$heteroalkyl, substituted $(C_{2-30})$acyl, substituted $(C_{2-30})$alkenyl, substituted $(C_{2-30})$alkynyl, substituted aryl$(C_{1-30})$alkyl, and substituted aryl$(C_{1-30})$acyl;

provided that when $R^2$ is $(C_{1-30})$acyl, aryl$(C_{1-30})$acyl, substituted $(C_{2-30})$acyl, or substituted aryl$(C_{1-30})$acyl, $R^3$ is H, $(C_{1-30})$alkyl, $(C_{1-30})$heteroalkyl, $(C_{2-30})$alkenyl, $(C_{2-30})$alkynyl, aryl$(C_{1-30})$alkyl, substituted $(C_{1-30})$alkyl, substituted $(C_{1-30})$heteroalkyl, substituted $(C_{2-30})$alkenyl, substituted $(C_{2-30})$alkynyl, or substituted aryl$(C_{1-30})$alkyl;

$R^4$ and $R^5$ each is, independently for each occurrence, H, $(C_{1-40})$alkyl, $(C_{1-40})$heteroalkyl, $(C_{1-40})$acyl, $(C_{2-40})$alkenyl, $(C_{2-40})$alkynyl, aryl$(C_{1-40})$alkyl, aryl$(C_{1-40})$acyl, substituted $(C_{1-40})$alkyl, substituted $(C_{1-40})$heteroalkyl, substituted $(C_{1-40})$acyl, substituted $(C_{2-40})$alkenyl, substituted $(C_{2-40})$alkynyl, substituted aryl$(C_{1-40})$alkyl, substituted aryl$(C_{1-40})$acyl, $(C_{1-40})$alkylsulfonyl, or C(NH)—NH$_2$, wherein when $R^4$ is $(C_{1-40})$acyl, aryl$(C_{1-40})$acyl, substituted $(C_{1-40})$acyl, substituted aryl$(C_{1-40})$acyl, $(C_{1-40})$alkylsulfonyl, or C(NH)—NH$_2$, then $R^5$ is H or $(C_1-C_{40})$alkyl, $(C_{1-40})$heteroalkyl, $(C_{2-40})$alkenyl, $(C_{2-40})$alkynyl, aryl$(C_{1-40})$alkyl, substituted $(C_{1-40})$alkyl, substituted $(C_{1-40})$heteroalkyl, substituted $(C_{2-40})$alkenyl, substituted $(C_{2-40})$alkynyl, or substituted aryl$(C_{1-40})$alkyl;

n is, independently for each occurrence, 1, 2, 3, 4, or 5;

$X^1, X^2, X^3, X^4$, and $X^5$ each is, independently for each occurrence, H, F, Cl, Br, I, $(C_{1-10})$alkyl, substituted $(C_{1-10})$alkyl, aryl, substituted aryl, OH, CH$_2$NH$_2$, NH$_2$, NO$_2$, or CN; and provided that the compound contains at least one substitution with an unnatural amino acid.

A subset (IA) of the compounds covered by the above formula I, are those in which:

$A^1$ is Tyr;
$A^2$ is Pro;
$A^3$ is Ser or Aib;
$A^4$ is Lys;
$A^5$ is Pro;
$A^6$ is Asp or Aib;
$A^7$ is Asn or Aib;
$A^8$ is Pro;
$A^9$ is Gly or Aib;
$A^{10}$ is Glu or Aib;
$A^{11}$ is Asp or Aib;
$A^{12}$ is Ala or Aib;
$A^{13}$ is Pro;
$A^{14}$ is Ala or Aib;
$A^{15}$ is Glu or Aib;
$A^{16}$ is Asp or Aib;
$A^{17}$ is Met, A6c, Aib, or Nle;
$A^{18}$ is Ala or Aib;
$A^{19}$ is Arg;
$A^{20}$ is Tyr;
$A^{21}$ Tyr;
$A^{22}$ is Ser or Aib;
$A^{23}$ is Ala or Aib;
$A^{24}$ is Leu or A6c;
$A^{25}$ is Arg;
$A^{26}$ is His;
$A^{27}$ is Tyr;
$A^{28}$ is Ile or A6c;
$A^{29}$ is Asn or Aib;
$A^{30}$ is Leu or A6c;
$A^{31}$ is Ile, A6c, or Leu;
$A^{32}$ is Thr or Aib;
$A^{33}$ is Arg;

$A^{34}$ is Dhp, 4Hyp, Inp, Nip, hPro, Tic, or HN—CH(($CH_2$)$_n$—N($R^4R^5$))—C(O);
$A^{35}$ is Arg, Apc, Lys, 4$NH_2$Phe, or 4$NH_2CH_2$Phe;
$A^{36}$ is Tyr or Aic;
$A^{37}$ is deleted;
$R^1$ is $NH_2$;
$R^2$ and $R^3$ each is, independently for each occurrence, H or ($C_{1-30}$)acyl;
provided that when $R^2$ is ($C_{1-30}$)acyl, $R^3$ is H;
$R^4$ and $R^5$ each is, independently for each occurrence, H or ($C_{1-40}$)acyl; n is 4; and
$X^1$, $X^2$, $X^3$, $X^4$, and $X^5$ each is, independently for each occurrence, H, $CH_2NH_2$, or $NH_2$.

In the formula (I) or the subset (IA), the peptide bond between $A^{35}$ and $A^{36}$ may be replaced by a pseudopeptide bond, wherein $A^{35}$-$A^{36}$ may be Lys-ψ($CH_2$—NH)Tyr or Lys-ψ($CH_2$—N(Ac))Tyr.

In the formula (I) or the subset (IA), $A^{34}$ is preferably 4Hyp.

In the formula (I) or the subset (IA), HN—CH(($CH_2$)$_n$—N($R^4R^5$))—C(O) is preferably Lys($N^\epsilon$—C(O)—($CH_2$)$_{12}$—$CH_3$).

Preferred compounds of the formula (I) or the subset (IA) are:

Example 1: [Aib$^{10}$, 4Hyp$^{34}$]hNPY(1-36)-$NH_2$; (SEQ ID NO: 3)

Example 2: [Aib$^{17}$, 4Hyp$^{34}$]hNPY(1-36)-$NH_2$; (SEQ ID NO: 4)

Example 3: [Aib$^{11,17}$, 4Hyp$^{34}$]hNPY(1-36)-$NH_2$; (SEQ ID NO: 5)

Example 4: [4Hyp$^{34}$]hNPY(1-36)-$NH_2$; (SEQ ID NO: 6)

Example 5: [Aib$^{22}$, 4Hyp$^{34}$]hNPY(1-36)-$NH_2$; (SEQ ID NO: 7)

Example 6: [A6c$^{31}$, 4Hyp$^{34}$]hNPY(1-36)-$NH_2$; (SEQ ID NO: 8)

Example 7: [A6c$^{30}$, 4Hyp$^{34}$]hNPY(1-36)-$NH_2$; (SEQ ID NO: 9)

Example 8: [A6c$^{28}$, 4Hyp$^{34}$]hNPY(1-36)-$NH_2$; (SEQ ID NO: 10)

Example 9: [Aib$^{3}$, 4Hyp$^{34}$]hNPY(1-36)-$NH_2$; (SEQ ID NO: 11)

Example 10: [A6c$^{24}$, 4Hyp$^{34}$]hNPY(1-36)-$NH_2$; (SEQ ID NO: 12)

Example 11: [Aib$^{6}$, 4Hyp$^{34}$]hNPY(1-36)-$NH_2$; (SEQ ID NO: 13)

Example 12: [Aib$^{18}$, 4Hyp$^{34}$]hNPY(1-36)-$NH_2$; (SEQ ID NO: 14)

Example 13: [Aib$^{29}$, 4Hyp$^{34}$]hNPY(1-36)-$NH_2$; (SEQ ID NO: 15)

Example 14: [Aib$^{32}$, 4Hyp$^{34}$]hNPY(1-36)-$NH_2$; (SEQ ID NO: 16)

Example 15: [Aib$^{23}$, 4Hyp$^{34}$]hNPY(1-36)-$NH_2$; (SEQ ID NO: 17)

Example 16: [A6c$^{17}$, 4Hyp$^{34}$]hNPY(1-36)-$NH_2$; (SEQ ID NO: 18)

Example 17: [Aib$^{11}$, 4Hyp$^{34}$]hNPY(1-36)-$NH_2$; (SEQ ID NO: 19)

Example 18: [Aib$^{12}$, 4Hyp$^{34}$]hNPY(1-36)-$NH_2$; (SEQ ID NO: 20)

Example 19: [Aib$^{14}$, 4Hyp$^{34}$]hNPY(1-36)-$NH_2$; (SEQ ID NO: 21)

Example 20: [Aib$^{15}$, 4Hyp$^{34}$]hNPY(1-36)-$NH_2$; (SEQ ID NO: 22)

Example 21: [Aib$^{16}$, 4Hyp$^{34}$]hNPY(1-36)-$NH_2$; (SEQ ID NO: 23)

Example 22: [Aib$^{7}$, 4Hyp$^{34}$]hNPY(1-36)-$NH_2$; (SEQ ID NO: 24)

-continued

Example 23: [Aib⁹, 4Hyp³⁴]hNPY(1-36)-NH₂; (SEQ ID NO: 25)

Example 24: [Aib¹⁰,¹⁷, 4Hyp³⁴]hNPY(1-36)-NH₂; (SEQ ID NO: 26)

Example 25: [Aib¹⁵,¹⁷, 4Hyp³⁴]hNPY(1-36)-NH₂; (SEQ ID NO: 27)

Example 26: [Aib¹¹,¹⁵, Nle¹⁷, 4Hyp³⁴]hNPY(1-36)-NH₂; (SEQ ID NO: 28)

Example 27: [Aib¹⁰,¹⁵, Nle¹⁷, 4Hyp³⁴]hNPY(1-36)-NH₂; (SEQ ID NO: 29)

Example 28: [Aib¹¹,¹⁵,¹⁷, 4Hyp³⁴]hNPY(1-36)-NH₂; (SEQ ID NO: 30)

Example 29: [Aib¹²,¹⁵,¹⁷, 4Hyp³⁴]hNPY(1-36)-NH₂; (SEQ ID NO: 31)

Example 30: [Aib¹⁰,¹⁵,¹⁷, 4Hyp³⁴]hNPY(1-36)-NH₂; (SEQ ID NO: 32)

Example 31: [Aib¹¹,¹⁶, 4Hyp³⁴]hNPY(1-36)-NH₂; (SEQ ID NO: 33)

Example 32: [Aib¹⁰,¹⁶, 4Hyp³⁴]hNPY(1-36)-NH₂; (SEQ ID NO: 34)

Example 33: [Aib¹¹,¹⁷, 4Hyp³⁴, Lys³⁵-ψ(CH₂—N(Ac))Tyr³⁶]hNPY(1-36)-NH₂; (SEQ ID NO: 35)

Example 34: [Aib¹⁷, 4Hyp³⁴, Apc³⁵]hNPY(1-36)-NH₂; (SEQ ID NO: 36)

Example 35: [Aib¹⁷, 4Hyp³⁴, Aic³⁶]hNPY(1-36)-NH₂; (SEQ ID NO: 37)

Example 36: [Aib¹⁷, 4Hyp³⁴, 4NH₂Phe³⁵]hNPY(1-36)-NH₂; (SEQ ID NO: 38)

Example 37: [Aib¹⁷, 4Hyp³⁴, 4NH₂CH₂Phe³⁵]hNPY(1-36)-NH₂; (SEQ ID NO: 39)

Example 38: [Aib¹⁷, 4Hyp³⁴, Lys³⁵-ψ(CH₂—NH)Tyr³⁶]hNPY(1-36)-NH₂; (SEQ ID NO: 40)

Example 39: [Aib¹¹,¹⁷, 4Hyp³⁴, Lys³⁵-ψ(CH₂—NH)Tyr³⁶]hNPY(1-36)-NH₂; (SEQ ID NO: 41)

Example 40: [Nip³⁴]hNPY(1-36)-NH₂; (SEQ ID NO: 42)

Example 41: [Inp³⁴]hNPY(1-36)-NH₂; (SEQ ID NO: 43)

Example 42: [Dhp³⁴]hNPY(1-36)-NH₂; (SEQ ID NO: 44)

Example 43: [hPro³⁴]hNPY(1-36)-NH₂; (SEQ ID NO: 45)

Example 44: [Tic³⁴]hNPY(1-36)-NH₂;
and (SEQ ID NO: 46)

Example 45: [Leu³¹, Lys³⁴(Nᵋ—C(O)—(CH₂)₁₂—CH₃)]hNPY(1-36)-NH₂. (SEQ ID NO: 47)

DETAILED DESCRIPTION OF THE INVENTION

As used herein the term "amino acid" refers to any natural or unnatural amino acid, including but not limited to α-amino acids, β-amino acids, or γ-amino acids, and may be either D- or L-amino acid unless otherwise indicated.

With the exception of the N-terminal amino acid, all amino acid abbreviations (e.g., Ala) in this disclosure have the structure —NH—C(R)(R')—CO—, wherein R and R' each is, independently, hydrogen or the side chain of an amino acid (e.g., R=$CH_3$ and R'=H for Ala), or R and R' may be joined to form a ring system. For the N-terminal amino acid, the abbreviation stands for the structure of $(R^2R^3)$—N—C(R)(R')—CO—, wherein $R^2$ and $R^3$ are as defined in the formula (I).

A peptide of this invention is also denoted by another format, e.g., [$Pro^3$]hNPY(1-36)-$NH_2$ (SEQ ID NO:48), with the substituted amino acids from the natural sequence placed between the brackets, e.g., Pro for Gln in hNPY. The designation "$NH_2$" in hNPY(1-36)-$NH_2$ (SEQ ID NO:1) indicates that the C-terminus of the peptide is amidated whereas hNPY (1-36)-OH (SEQ ID NO:49) indicates the free acid form.

The following list of some of the abbreviations used in the present application is provided for ease of reference, however, any abbreviation used in the instant application not defined herein are not used contrary to the recognized meanings thereof.

Abu α-aminobutyric acid
Acc 1-amino-1-cyclo($C_{3-9}$)alkyl carboxylic acid, wherein
    A3c represents 1-amino-1-cyclopropanecarboxylic acid;
    A4c represents 1-amino-1-cyclobutanecarboxylic acid;
    A5c represents 1-amino-1-cyclopentanecarboxylic acid; and
    A6c represents 1-amino-1-cyclohexanecarboxylic acid
Adc 10-aminodecanoic acid
Ado 12-aminododecanoic acid
Ahp 7-aminoheptanoic acid
Ahx 6-aminohexanoic acid
Aib α-aminoisobutyric acid
Aic 2-aminoindan-2-carboxylic acid
Ala or A alanine
Anc 9-aminononanoic acid
Aoc 8-aminooctanoic acid
Apc 4-amino-4-carboxypiperidine, represented by structure:

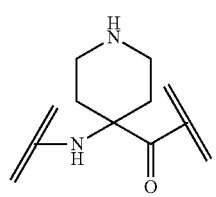

wherein, the parallel lines "=" indicate points of attachment of the moiety to another moiety or sequence.
Apn 5-aminopentanoic acid
Arg or R arginine
hArg homoarginine
Asn or N asparagine
Asp or D aspartic acid
Aun 11-aminoundecanoic acid
Cha β-cyclohexylalanine
Cys or C cysteine
Dab 2,4-diaminobutyric acid
Dap 2,3-diaminopropionic acid
Dhp 3,4-dehydroproline
Dmt 5,5-dimethylthiazolidine-4-carboxylic acid
Gaba 4-aminobutyric acid
Gln or Q glutamine
Glu or E glutamic acid
Gly or G glycine
His or H histidine
3Hyp trans-3-hydroxy-L-proline, i.e., (2S,3S)-3-hydroxy-pyrrolidine-2-carboxylic acid
cis-3Hyp cis-3-hydroxy-L-proline, i.e., (2S,3R)-3-hydroxypyrrolidine-2-carboxylic acid
4Hyp 4-hydroxyproline, i.e., (2S,4R)-4-hydroxypyrrolidine-2-carboxylic acid
cis-4Hyp cis-4-hydroxy-L-proline, i.e., (2S,4S)-4-hydroxypyrrolidine-2-carboxylic acid
Ile or I isoleucine
Inc indoline-2-carboxylic acid
Inp isonipecotic acid
Ktp 4-ketoproline
Leu or L leucine
hLeu homoleucine
Lys or K lysine
Met or M methionine
Nip nipecotic acid
Nle norleucine
$N^\epsilon$ indicates that the entity within the parentheses is coupled to the epsilon-nitrogen of the Lys sidechain
Nva norvaline
Oic octahydroindole-2-carboxylic acid
Orn ornithine
2-Pal β-(2-pyridyl)alanine
3-Pal β-(3-pyridyl)alanine
4-Pal β-(4-pyridyl)alanine
Phe or F phenylalanine
hPhe homophenylalanine
$4NH_2CH_2$Phe 4-aminomethyl-phenylalanine
$4NH_2$Phe 4-amino-phenylalanine
Pro or P proline
hPro homoproline
Sar sarcosine or N-methyl glycine
Ser or S serine
Thr or T threonine
Tic 1,2,3,4-tetrahydroisoquinoline-3-carboxylic acid
Tle tert-leucine
Val or V valine Certain other abbreviations used herein are defined as follows:

Ac acetyl
Aloc allyloxycarbonyl
Boc tert-butyloxycarbonyl
Bhoc benzhydryloxycarbonyl
BSA bovine serum albumin
Bzl benzyl
DCM dichloromethane
Dde 1-(4,4-dimethyl-2,6-dioxocyclohex-1-ylidine)ethyl
DIC N,N-diisopropylcarbodiimide
DIEA: diisopropylethyl amine
Dmab 4-{N-(1-(4,4-dimethyl-2,6-dioxocyclohexylidene)-3-methylbutyl)-amino}benzyl
DMAP 4-(dimethylamino)pyridine
DMF dimethylformamide
DNP 2,4-dinitrophenyl
EMEM Eagle's minimal essential medium
et ethyl
Fmoc fluorenylmethyloxycarbonyl HATU O-(7-azabenzotriazole-1-yl)-1,1,3,3-tetramethyluronium hexafluorophosphate
HBTU 2-(1H-benzotriazole-1-yl)-1,1,3,3-tetramethyluronium hexafluorophosphate
cHex cyclohexyl
HOAT O-(7-azabenzotriazol-1-yl)-1,1,3,3-tetramethyluronium hexafluorophosphate
HOBt 1-hydroxy-benzotriazole
HPLC high performance liquid chromatography
MBHA 4-methylbenzhydrylamine
Mmt 4-methoxytrityl
NMP N-methyl-2-pyrrolidinone
Pbf 2,2,4,6,7-pentamethyldihydrobenzofuran-5-sulfonyl
tBu tert-butyl
TIS triisopropylsilane
TOS tosyl
Trt trityl
TFA trifluoro acetic acid
TFFH tetramethylfluoroforamidinium hexafluorophosphate
Lys-ψ(CH$_2$—NH)Tyr has the structure of:

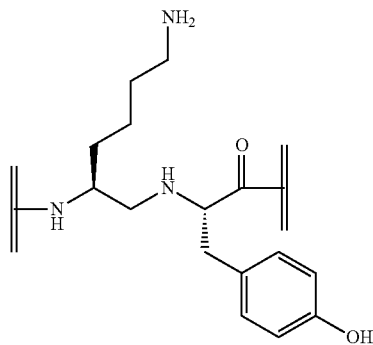

The Greek letter psi "ψ" is used herein to indicate that a peptide bond has been replaced by a pseudopeptide bond. In an amino acid sequence name, the format of the ψ term is A-ψ(X-X')-B wherein A is the amino acyl radical whose carbonyl group has been modified to X and B the amino acyl radical whose α-amino groups has been modified to X'. X and X' are shown as strings of element symbols, separated by a bond, e.g., Lys-ψ(CH$_2$—NH)-Tyr.

"Alkyl" refers to a hydrocarbon group containing one or more carbon atoms, where multiple carbon atoms if present are joined by single bonds, examples of which include but are not limited to methyl, ethyl, propyl and butyl. The alkyl hydrocarbon group may be straight-chain or contain one or more branches or cyclic groups, examples of which include, but are not limited to, isopropyl and tertbutyl.

"Substituted alkyl" refers to an alkyl wherein one or more hydrogen atoms of the hydrocarbon group are replaced with one or more substituents selected from the group consisting of halogen, (i.e., fluorine, chlorine, bromine, and iodine), OH, CN, SH, NH$_2$, NHCH$_3$, NO$_2$, (C$_{1-2}$)alkyl substituted with 1 to 6 halogens, CF$_3$, OCH$_3$, OCF$_3$, and (CH$_2$)$_{0-4}$—COOH. In different embodiments, 1, 2, 3 or 4 substituents are present. The presence of (CH$_2$)$_{0-4}$—COOH results in the production of an alkyl acid. Examples of alkyl acids containing (CH$_2$)$_{0-4}$—COOH include, but are not limited to, 2-norbornane acetic acid, tert-butyric acid and 3-cyclopentyl propionic acid.

"Heteroalkyl" refers to an alkyl wherein one of more of the carbon atoms in the hydrocarbon group are replaced with one or more of the following atoms or groups: amino, amido, O, S, N, and carbonyl. In different embodiments, 1 or 2 heteroatoms are present.

"Substituted heteroalkyl" refers to a heteroalkyl wherein one or more hydrogen atoms of the hydrocarbon group are replaced with one or more substituents selected from the group consisting of halogen, (i.e., fluorine, chlorine, bromine, and iodine), OH, CN, SH, NH$_2$, NHCH$_3$, NO$_2$, (C$_{1-2}$)alkyl substituted with 1 to 6 halogens, CF$_3$, OCH$_3$, OCF$_3$, and (CH$_2$)$_{0-4}$—COOH. In different embodiments, 1, 2, 3 or 4 substituents are present.

"Alkenyl" refers to a hydrocarbon group made up of two or more carbons where one or more carbon-carbon double bonds are present, examples of which include, but are not limited to, vinyl, allyl, butenyl and propenyl. The alkenyl hydrocarbon group may be straight-chain or contain one or more branches or cyclic groups, examples of which include, but are not limited to, n-butenyl versus t-butenyl, and n-pentenyl compared to cyclopentenyl.

"Substituted alkenyl" refers to an alkenyl wherein one or more hydrogens are replaced with one or more substituents selected from the group consisting of halogen (i.e., fluorine, chlorine, bromine, and iodine), OH, CN, SH, NH$_2$, NHCH$_3$, NO$_2$, (C$_{1-2}$)alkyl substituted with 1 to 6 halogens, CF$_3$, OCH$_3$, OCF$_3$, and (CH$_2$)$_{0-4}$—COOH. In different embodiments, 1, 2, 3 or 4 substituents are present.

"Aryl" refers to an optionally substituted aromatic group with at least one ring having a conjugated π-electron system containing up to two conjugated or fused ring systems. Aryl includes, but is not limited to, carboxylic aryl, heterocyclic aryl and biaryl groups. Preferably, an aryl is a 5- or 6-membered ring. Preferred atoms for a heterocyclic aryl include, but are not limited to, one or more of sulfur, oxygen and nitrogen. Examples of aryl include, but are not limited to, phenyl, 1-naphthyl, 2-naphthyl, indole, quinoline, 2-imidazole, and 9-anthracene. Aryl substituents are selected from the group consisting of (C$_{1-4}$ alkyl, (C$_{1-4}$ alkoxy, halogen (i.e., fluorine, chlorine, bromine, and iodine), OH, CN, SH, NH$_2$, NO$_2$, (C$_{1-2}$)alkyl substituted with 1 to 5 halogens, CF$_3$, OCF$_3$, and (CH$_2$)$_{0-4}$—COOH. In different embodiments, aryl contains 0, 1, 2, 3 or 4 substituents.

"Alkylaryl" refers to an "alkyl" joined to an "aryl," as defined above.

The term "cycloalkyl" is intended to include a mono-cycloalkyl group or a bi-cycloalkyl group of the indicated carbon number known to those of skill in the art.

The term "heterocycle" includes mono-cyclic and bi-cyclic systems having one or more heteroatoms, such as oxygen, nitrogen and sulfur. The ring systems may be aromatic, for example, pyridine, indole, quinoline, pyrimidine, thiophene (also known as thienyl), furan, benzothiophene, tetrazole, dihydroindole, indazole, N-formylindole, benzimidazole, thiazole, and thiadiazole. The ring systems also may be non-aromatic, for example, but not limited to, pyrrolidine, piperidine, morpholine, and the like.

Synthesis

The compounds of this invention can be and were produced using the techniques disclosed in the examples herein as well as techniques that are well known in the art. For example, a polypeptide region of an NPY analogue can be chemically or biochemically synthesized and/or modified. See, e.g., Stewart, J. M., et al., *Solid Phase Synthesis*, Pierce Chemical Co., 2d ed. (1984); and see, e.g., Sambrook et al., *Molecular Cloning, A Laboratory Manual*, 2$^{nd}$ ed., Cold Spring Harbor Laboratory Press (1989) for examples of techniques for biochemical synthesis involving the introduction of a nucleic acid into a cell and expression of nucleic acids.

The examples are provided for the purpose of illustration and are not meant to limit the scope of the present invention in any manner.

EXAMPLE 1

[Aib$^{10}$, 4HyP$^{34}$]hNPY(1-36)-NH$_2$

The titled peptide was assembled using Fmoc-chemistry. The C-terminal portion of the peptide (residues 18-36) was synthesized on ABI 433A Peptide Synthesizer (Applied Biosystems, Foster City, Calif., USA) at the 1.0 mmole scale. The reaction vessel containing 1.37 g of 0.73 mmol/Rink Amide MBHA resin (Novabiochem, San Diego, Calif., USA) was placed in a reaction vessel. The resin was then treated with 10 ml of NMP for 15 minutes to swell the resin. The ABI Fast-Moc 1.0® protocol was used to generate the peptide.

Each cycle comprised of deblocking the N-terminal Fmoc using 20% piperidine followed by extensive NMP washing. Pre-packaged 1.0 mmole cartridges of each amino acid were then dissolved in 0.45M HOBT/HBTU. After enough time was allotted for dissolution of the amino acid, it was automatically transferred to the activation vessel. Two more 1.0 mmole amino acid cartridges were dissolved and transferred to the activation vessel for a total of 3 equivalents of amino acid used per coupling step. DIPEA, 3 ml of a 2M solution, was then introduced to the activation vessel for a total of 6 eq. DIPEA.

This entire mixture was then introduced to the resin and allowed to mix for 15 minutes. The reaction vessel was emptied, washed with NMP and then followed by a second coupling step. Following the second coupling step, the resin was again thoroughly washed. Each amino acid was double-coupled in a similar fashion. Following the coupling step of the first Tyr residue, for each of the next 4 coupling steps, and each Arg coupling step, the resin was capped with 5 ml of capping solution (0.5M acetic anhydride/0.13M DIPEA/0.01M HOBT) to block any unacylated resin sites. The following amino acid cartridges were used for the coupling steps: Cycle 1) Fmoc-Tyr(tBu)-OH; Cycle 2) Fmoc-Arg(Pbf)-OH; Cycle 3) Fmoc-4Hyp-OH; Cycle 4) Fmoc-Arg(Pbf)-OH; Cycle 5) Fmoc-Thr(tBu)-OH; Cycle 6) Fmoc-Ile-OH; Cycle 7) Fmoc-Leu-OH; Cycle 8) Fmoc-Asn(Trt)-OH; Cycle 9) Fmoc-Ile-OH; Cycle 10) Fmoc-Tyr(tBu)-OH; Cycle 11) Fmoc-His(Trt)-OH; Cycle 12) Fmoc-Arg(Pbf)-OH; Cycle 13) Fmoc-Leu-OH; Cycle 14) Fmoc-Ala-OH; Cycle 15) Fmoc-Ser(tBu)-OH; Cycle 16) Fmoc-Tyr(tBu)-OH; Cycle 17) Fmoc-Tyr(tBu)-OH; Cycle 18) Fmoc-Arg(Pbf)-OH; and Cycle 19) Fmoc-Ala-OH. Following the last coupling cycle, the resin was washed with NMP, followed by standard N-terminal Fmoc deblocking, washed with NMP followed by DCM.

Following assembly of the C-terminal portion of the peptide backbone (residues 18-36), only one tenth of the resin (0.1 mmole) was used to construct the N-terminal portion of the peptide, with the remainder saved. The N-terminal portion of the titled peptide (residues 1-17) was constructed using microwave-assisted Fmoc Chemistry on Liberty Peptide Synthesizer (CEM, Matthews, N.C., USA) at the 0.1 mmole scale. The resin from the previous synthesis was placed in a 50 ml conical tube along with 15 ml of DMF and loaded onto a resin position on the synthesizer. The resin was then quantitatively transferred to the reaction vessel via the automated process. The standard Liberty synthesis protocol for 0.1 mmole scale synthesis was used. This protocol involves deprotecting the N-terminal Fmoc moiety via an initial treatment with 7 ml of 20% piperidine, containing 0.1M HOBT, in DMF. The initial deprotection step was for 30 seconds with microwave power (45 watts, maximum temperature of 75° C.), and nitrogen bubbling (3 seconds on/7 seconds off). The reaction vessel was then drained and a second piperidine treatment, identical to the first treatment, except that it was for a 3-minute duration.

The resin was then drained and thoroughly washed with DMF several times. The protected amino acid, Fmoc-Met-OH, prepared as 0.2M stock solution in DMF, was then added (2.5 ml, 5 equivalents), followed by 1.0 ml of 0.45M (4.5 eq.) HBTU in DMF. This was followed by the addition of 0.5 ml of 2M (10 eq.) DIPEA in NMP. The coupling step was performed for 5 minutes using 20 watts of microwave power, a maximum temperature of 75° C., and the same rate of nitrogen bubbling. Following the initial coupling step, the reaction vessel was drained to waste and the coupling step repeated.

Cycle 2 was then initiated similar to Cycle 1. All amino acids were introduced similarly and a double-coupling strategy was employed throughout the entire sequence. Residues 9-10 (Gly-Aib) contained a capping procedure immediately following the coupling step. Capping was performed by adding 7 ml of 0.5M acetic anhydride, containing 0.015M HOBT in NMP, along with 2 ml of the 2M DIPEA solution using a multi-step microwave protocol: 50 watts of power for 30 seconds (65° C. maximum temperature), followed by 30 seconds of microwave power off, followed by a second round of 30 seconds of microwave power on (50 watts), and then again 30 seconds of no microwave power. The resin was then drained and thoroughly washed with DMF. The following amino acids (Advanced Chemtech, Louisville, Ky., USA) were used: Cycle 20) Fmoc-Met-OH; Cycle 21) Fmoc-Asp(OtBu)-OH; Cycle 22) Fmoc-Glu(OtBu)-OH; Cycle 23) Fmoc-Ala-OH; Cycle 24) Fmoc-Pro-OH; Cycle 25) Fmoc-Ala-OH; Cycle 26) Fmoc-Asp(OtBu)-OH; Cycle 27) Fmoc-Aib-OH; Cycle 28) Fmoc-Gly-OH; Cycle 29) Fmoc-Pro-OH; Cycle 30) Fmoc-Asn(Trt)-OH; Cycle 31) Fmoc-Asp(OtBu)-OH; Cycle 32) Fmoc-Pro-OH; Cycle 33) Fmoc-Lys(Boc)-OH; Cycle 34) Fmoc-Ser(tBu)-OH; Cycle 35) Fmoc-Pro-OH; Cycle 36) Fmoc-Tyr(tBu)-OH.

Once the peptide backbone was complete, standard piperidine treatment was used to remove the N-terminal Fmoc group using the standard deprotection procedure described previously. The resin was then thoroughly washed with DMF and then transferred back to the 50 ml conical tube using DMF as the transfer solvent.

The resin was deprotected and cleaved from the resin via treatment with 5 ml of the following reagent: 5% TIS, 2% water, 5% (w/v) DTT, and 88% TFA, and allowed to mix for 3.5 hours. The filtrate was collected into 45 ml of cold anhydrous ethyl ether. The precipitate was pelleted for 10 minutes at 3500 RPM in a refrigerated centrifuge. The ether was decanted and the peptide re-suspended in fresh ether. The ether workup was performed a total of 2 times. Following the last ether wash, the peptide was allowed to air dry to remove residual ether. The peptide pellet was resuspended in 8 ml of acetonitrile followed by 8 ml of de-ionized water and allowed to fully dissolve.

The peptide solution was then analyzed by mass spectrometry. Mass analysis employing electrospray ionization identified a main product containing a mass of 4212.1, corresponding to the desired product. Analytical HPLC analysis, employing a 250×4.6 mm C18 column (Phenomenex, Torrance, Calif., USA) using a gradient of 2-60% acetonitrile (0.1% TFA) over 30 minutes, identified a main product with 45% purity. The crude peptide was then purified on a preparative HPLC equipped with a C18 reverse phase column using a 10-60% acetonitrile (0.1% TFA) over 50 minutes at a 10 ml/min flow rate. The purified product was analyzed by HPLC for purity (>99%) and mass spectrometry (4212.8 da), with the experimental mass corresponding well to the expected mass of 4212.7. The peptide was subsequently lyophilized producing 39 mg of purified product representing a 9% yield.

EXAMPLE 2

[Aib$^{17}$, 4Hyp$^{34}$]hNPY(1-36)-NH$_2$

The titled peptide was assembled using Fmoc-chemistry. The C-terminal portion of the peptide (residues 18-36) was synthesized on ABI 433A Peptide Synthesizer (Applied Biosystems, Foster City, Calif., USA) at the 1.0 mmole scale. The reaction vessel containing 1.37 g of 0.73 mmol/Rink Amide MBHA resin (Novabiochem, San Diego, Calif., USA) was placed in a reaction vessel. The resin was then treated with 10 ml of NMP for 15 minutes to swell the resin. The ABI Fast-Moc 1.0® protocol was used to generate the peptide.

Each cycle comprised deblocking the N-terminal Fmoc using 20% piperidine followed by extensive NMP washing. Pre-packaged 1.0 mmole cartridges of each amino acid were then dissolved in 0.45M HOBT/HBTU. After the amino acid had dissolved, it was automatically transferred to the activation vessel. Two more 1.0 mmole amino acid cartridges were dissolved and transferred to the activation vessel for a total of 3 equivalents of amino acid used per coupling step. DIPEA, 3 ml of a 2M solution, was then introduced to the activation vessel for a total of 6 eq. DIPEA.

This entire mixture was then introduced to the resin and allowed to mix for 15 minutes. The reaction vessel was emptied, washed with NMP, and then followed by a second coupling step. Following the second coupling step, the resin was again thoroughly washed. Each amino acid was double-coupled in a similar fashion. Following the coupling step of the first Tyr residue, for each of the next four coupling steps and each Arg coupling step, the resin was capped with 5 ml of capping solution (0.5M acetic anhydride/0.13M DIPEA/0.01M HOBT) to block any unacylated resin sites. The following amino acid cartridges were used for the coupling steps: Cycle 1) Fmoc-Tyr(tBu)-OH; Cycle 2) Fmoc-Arg(Pbf)-OH; Cycle 3) Fmoc-4Hyp-OH; Cycle 4) Fmoc-Arg(Pbf)-OH; Cycle 5) Fmoc-Thr(tBu)-OH; Cycle 6) Fmoc-Ile-OH; Cycle 7) Fmoc-Leu-OH; Cycle 8) Fmoc-Asn(Trt)-OH; Cycle 9) Fmoc-Ile-OH; Cycle 10) Fmoc-Tyr(tBu)-OH; Cycle 11) Fmoc-His(Trt)-OH; Cycle 12) Fmoc-Arg(Pbf)-OH; Cycle 13) Fmoc-Leu-OH; Cycle 14) Fmoc-Ala-OH; Cycle 15) Fmoc-Ser(tBu)-OH; Cycle 16) Fmoc-Tyr(tBu)-OH; Cycle 17) Fmoc-Tyr(tBu)-OH; Cycle 18) Fmoc-Arg(Pbf)-OH; and Cycle 19) Fmoc-Ala-OH.

Following the last coupling cycle, the resin was washed with NMP, followed by standard N-terminal Fmoc deblocking and washed with NMP followed by DCM. After assembling the C-terminal portion of the peptide backbone (residues 18-36), one tenth of the resin (0.1 mmole) was used to construct the N-terminal portion of the peptide, with the remainder conserved. The N-terminal portion of the titled peptide (residues 1-17) was constructed using microwave-assisted Fmoc Chemistry on a Liberty Peptide Synthesizer (CEM, Matthews, N.C., USA) at the 0.1 mmole scale. The resin from the previous synthesis was placed in a 50 ml conical tube along with 15 ml of DMF and loaded onto a resin position on the synthesizer. The resin was then quantitatively transferred to the reaction vessel via the automated process.

The standard Liberty synthesis protocol for 0.1 mmole scale synthesis was used involving deprotecting the N-terminal Fmoc moiety via an initial treatment with 7 ml of 20% piperidine containing 0.1M HOBT in DMF. The initial deprotection step lasted 30 seconds with microwave power (45 watts, maximum temperature of 75° C.) and nitrogen bubbling (3 seconds on/7 seconds off). The reaction vessel was then drained and a second piperidine treatment, identical to the first treatment was applied for 3 minutes. The resin was then drained and thoroughly washed with DMF several times. The protected amino acid, Fmoc-Aib-OH prepared as 0.2M stock solution in DMF, was then added (2.5 ml, 5 equivalents) followed by 1.0 ml of 0.45M (4.5 eq.) HBTU in DMF. This was followed by the addition of 0.5 ml of 2M (10 eq.) DIPEA in NMP. The coupling step was performed for 5 minutes using 20 watts of microwave power, at a maximum temperature of 75° C., and the same rate of nitrogen bubbling. Following the initial coupling step, the reaction vessel was drained to waste and the coupling step repeated.

Cycle 2 which was similar to Cycle 1 was then initiated. All amino acids were introduced similarly and a double-coupling strategy was employed throughout the entire sequence. Residues 16-17 (Asp-Aib) contained a capping procedure immediately following the coupling step. Capping was performed by adding 7 ml of 0.5M acetic anhydride containing 0.015M HOBT in NMP along with 2 ml of the 2M DIPEA solution using a multi-step microwave protocol: 50 watts of power for 30 seconds (65° C. maximum temperature), followed by 30 seconds of microwave power off, followed by a second round of 30 seconds of microwave power on (50 watts), and then again 30 seconds of no microwave power. The resin was then drained and thoroughly washed with DMF. The following amino acids (Advanced Chemtech, Louisville, Ky., USA) were used: Cycle 20) Fmoc-Aib-OH; Cycle 21) Fmoc-Asp(OtBu)-OH; Cycle 22) Fmoc-Glu(OtBu)-OH; Cycle 23) Fmoc-Ala-OH; Cycle 24) Fmoc-Pro-OH; Cycle 25) Fmoc-Ala-OH; Cycle 26) Fmoc-Asp(OtBu)-OH; Cycle 27) Fmoc-Glu(OtBu)-OH; Cycle 28) Fmoc-Gly-OH; Cycle 29) Fmoc-Pro-OH; Cycle 30) Fmoc-Asn(Trt)-OH; Cycle 31) Fmoc-Asp(OtBu)-OH; Cycle 32) Fmoc-Pro-OH; Cycle 33) Fmoc-Lys(Boc)-OH; Cycle 34) Fmoc-Ser(tBu)-OH; Cycle 35) Fmoc-Pro-OH; and Cycle 36) Fmoc-Tyr(tBu)-OH.

Once the peptide backbone was complete, standard piperidine treatment was used to remove the N-terminal Fmoc group using the standard deprotection procedure described previously. The resin was then thoroughly washed with DMF and then transferred back to the 50 ml conical tube using DMF as the transfer solvent.

The resin was deprotected and cleaved from the resin via treatment with 5 ml of the following reagent: 5% TIS, 2% water, 5% (w/v) DTT, and 88% TFA, and allowed to mix for 3.5 hours. The filtrate was collected into 45 ml of cold anhydrous ethyl ether. The precipitate was pelleted for 10 minutes at 3500 RPM in a refrigerated centrifuge. The ether was decanted and the peptide re-suspended in fresh ether. The ether workup was performed a total of 2 times. Following the last ether wash, the peptide was allowed to air dry to remove residual ether. The peptide pellet was resuspended in 8 ml of acetonitrile followed by 8 ml of de-ionized water and allowed to fully dissolve.

The peptide solution was then analyzed by mass spectrometry. Mass analysis employing electrospray ionization identified a main product containing a mass of 4210.8, corresponding to the desired product. Analytical HPLC analysis, employing a 250×4.6 mm C18 column (Phenomenex, Torrance, Calif., USA) using a gradient of 2-60% acetonitrile (0.1% TFA) over 30 minutes, identified a main product with 54% purity. The crude peptide was then purified on a preparative HPLC equipped with a C18 reverse phase column using a 10-60% acetonitrile (0.1% TFA) over 50 minutes at a 10 ml/min flow rate. The purified product was analyzed by HPLC for purity (>99%) and mass spectrometry (4210.6 da) with the experimental mass corresponding to the expected mass of 4210.6. The peptide was subsequently lyophilized producing 53 mg of purified product representing a 13% yield.

EXAMPLE 3

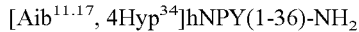
[Aib$^{11,17}$, 4Hyp$^{34}$]hNPY(1-36)-NH$_2$

The titled peptide was assembled using Fmoc-chemistry. The C-terminal portion of the peptide (residues 18-36) was synthesized on ABI 433A Peptide Synthesizer (Applied Biosystems, Foster City, Calif., USA) at the 1.0 mmole scale. The reaction vessel containing 1.37 g of 0.73 mmol/Rink Amide MBHA resin (Novabiochem, San Diego, Calif., USA) was placed in a reaction vessel. The resin was then treated with 10 ml of NMP for 15 min to swell the resin. The ABI FastMoc 1.0® protocol was used to generate the peptide.

Each cycle was comprised of deblocking the N-terminal Fmoc using 20% piperidine followed by extensive NMP washing. Pre-packaged 1.0 mmole cartridges of each amino acid were then dissolved in 0.45M HOBT/HBTU. After the amino acid had dissolved, it was automatically transferred to the activation vessel. Two more 1.0 mmole amino acid cartridges were dissolved and transferred to the activation vessel for a total of 3 equivalents of amino acid used per coupling step. DIPEA, 3 ml of a 2M solution, was then introduced to the activation vessel for a total of 6 eq. DIPEA.

This entire mixture was then introduced to the resin and allowed to mix for 15 minutes. The reaction vessel was emptied, washed with NMP, and then followed by a second coupling step. Following the second coupling step, the resin was again thoroughly washed. Each amino acid was double-coupled in a similar fashion. Following the coupling step of the first Tyr residue, for each of the next 4 coupling steps and each Arg coupling step, the resin was capped with 5 ml of capping solution (0.5M acetic anhydride/0.13M DIPEA/0.01M HOBT) to block any unacylated resin sites. The following amino acid cartridges were used for the coupling steps: Cycle 1) Fmoc-Tyr(tBu)-OH; Cycle 2) Fmoc-Arg(Pbf)-OH; Cycle 3) Fmoc-4Hyp-OH; Cycle 4) Fmoc-Arg(Pbf)-OH; Cycle 5) Fmoc-Thr(tBu)-OH; Cycle 6) Fmoc-Ile-OH; Cycle 7) Fmoc-Leu-OH; Cycle 8) Fmoc-Asn(Trt)-OH; Cycle 9) Fmoc-Ile-OH; Cycle 10) Fmoc-Tyr(tBu)-OH; Cycle 11) Fmoc-His(Trt)-OH; Cycle 12) Fmoc-Arg(Pbf)-OH; Cycle 13) Fmoc-Leu-OH; Cycle 14) Fmoc-Ala-OH; Cycle 15) Fmoc-Ser(tBu)-OH; Cycle 16) Fmoc-Tyr(tBu)-OH; Cycle 17) Fmoc-Tyr(tBu)-OH; Cycle 18) Fmoc-Arg(Pbf)-OH; and Cycle 19) Fmoc-Ala-OH. Following the last coupling cycle, the resin was washed with NMP, deblocked by standard N-terminal Fmoc deblocking, and again washed with NMP followed by DCM.

Following assembly of the C-terminal portion of the peptide backbone (residues 18-36), only one tenth of the resin (0.1 mmole) was used to construct the N-terminal portion of the peptide with the remainder saved. The N-terminal portion of the titled peptide (residues 1-17) was constructed using microwave-assisted Fmoc Chemistry on a Liberty Peptide Synthesizer (CEM, Matthews, N.C., USA) at the 0.1 mmole scale. The resin from the previous synthesis was placed in a 50 ml conical tube along with 15 ml of DMF and loaded onto a resin position on the synthesizer. The resin was then quantitatively transferred to the reaction vessel via the automated process. The standard Liberty synthesis protocol for 0.1 mmole scale synthesis was used. This protocol involves deprotecting the N-terminal Fmoc moiety via an initial treatment with 7 ml of 20% piperidine containing 0.1M HOBT in DMF. The initial deprotection step lasted 30 seconds with microwave power (45 watts, maximum temperature of 75° C.) and nitrogen bubbling (3 seconds on/7 seconds off). The reaction vessel was then drained and a second piperidine treatment, identical to the first treatment except that it was for a 3-minute duration was applied. The resin was then drained and thoroughly washed with DMF several times. The protected amino acid, Fmoc-Aib-OH prepared as 0.2M stock solution in DMF, was then added (2.5 ml, 5 equivalents) followed by 1.0 ml of 0.45M (4.5 eq.) HBTU in DMF. This was followed by the addition of 0.5 ml of 2M (10 eq.) DIPEA in NMP. The coupling step was performed for 5 minutes using 20 watts of microwave power at a maximum temperature of 75° C. and the same rate of nitrogen bubbling. Following the initial coupling step, the reaction vessel was drained to waste and the coupling step repeated.

Cycle 2 which was similar to Cycle 1 was then initiated. All amino acids were introduced similarly and a double-coupling strategy was employed throughout the entire process. Residues 10-11 and 16-17 (Glu-Aib and Asp-Aib) contained a capping procedure immediately following each coupling step. Capping was performed by adding 7 ml of 0.5M acetic anhydride containing 0.015M HOBT in NMP along with 2 ml of the 2M DIPEA solution using a multi-step microwave protocol: 50 watts of power for 30 seconds (65° C. max temperature), followed by 30 seconds of microwave power off, followed by a second round of 30 seconds of microwave power on (50 watts), and then again 30 seconds of no microwave power. The resin was then drained and thoroughly washed with DMF. The following amino acids (Advanced Chemtech, Louisville, Ky., USA) were used: Cycle 20) Fmoc-Aib-OH; Cycle 21) Fmoc-Asp(OtBu)-OH; Cycle 22) Fmoc-Glu(OtBu)-OH; Cycle 23) Fmoc-Ala-OH; Cycle 24) Fmoc-Pro-OH; Cycle 25) Fmoc-Ala-OH; Cycle 26) Fmoc-Aib-OH; Cycle 27) Fmoc-Glu(OtBu)-OH; Cycle 28) Fmoc-Gly-OH; Cycle 29) Fmoc-Pro-OH; Cycle 30) Fmoc-Asn(Trt)-OH; Cycle 31) Fmoc-Asp(OtBu)-OH; Cycle 32) Fmoc-Pro-OH; Cycle 33) Fmoc-Lys(Boc)-OH; Cycle 34) Fmoc-Ser(tBu)-OH; Cycle 35) Fmoc-Pro-OH; and Cycle 36) Fmoc-Tyr(tBu)-OH.

Once the peptide backbone was complete, a standard piperidine treatment was used to remove the N-terminal Fmoc group using the standard deprotection procedure described previously. The resin was then thoroughly washed with DMF and then transferred back to the 50 ml conical tube using DMF as the transfer solvent.

The resin was deprotected and cleaved from the resin via treatment with 5 ml of the following reagent: 5% TIS, 2% water, 5% (w/v) DTT, and 88% TFA, and allowed to mix for 3.5 hours. The filtrate was collected into 45 ml of cold anhydrous ethyl ether. The precipitate was pelleted for 10 minutes at 3500 RPM in a refrigerated centrifuge. The ether was decanted and the peptide re-suspended in fresh ether. The ether workup was performed a total of 2 times. Following the last ether wash, the peptide was allowed to air dry to remove residual ether. The peptide pellet was resuspended in 8 ml of acetonitrile followed by 8 ml of de-ionized water and allowed to fully dissolve.

The peptide solution was then analyzed by mass spectrometry. Mass analysis employing electrospray ionization identified a main product containing a mass of 4180.7, corresponding to the desired product. Analytical HPLC analysis, employing a 250×4.6 mm C18 column (Phenomenex, Torrance, Calif., USA) using a gradient of 2-60% acetonitrile (0.1% TFA) over 30 minutes identified a main product with 68% purity. The crude peptide was then purified on a preparative HPLC equipped with a C18 reverse phase column using a 10-60% acetonitrile (0.1% TFA) over 50 minutes at a 10 ml/min flow rate. The purified product was analyzed by HPLC for purity (>99%) and mass spectrometry (4180.5 da), with the experimental mass corresponding to the expected mass of 4180.6. The peptide was subsequently lyophilized producing 53 mg of purified product representing a 13% yield.

Other compounds of the invention can be prepared by a person of ordinary skill in the art using synthetic procedures analogous to those disclosed in the foregoing examples. Physical data for the compounds exemplified herein are given in Table 1.

TABLE 1

| Example Number | Mol. Wt. (Expected) | Mol. Wt. (ESI-MS) | % Purity (HPLC) |
| --- | --- | --- | --- |
| 1 | 4212.7 | 4212.8 | 99.9 |
| 2 | 4210.6 | 4210.6 | 99.9 |
| 3 | 4180.6 | 4180.5 | 99.9 |
| 4 | 4256.7 | 4257.3 | 98.2 |
| 5 | 4254.7 | 4255.0 | 98.7 |
| 6 | 4268.7 | 4268.9 | 98.8 |
| 7 | 4268.7 | 4268.7 | 97.3 |
| 8 | 4268.7 | 4268.9 | 96.7 |
| 9 | 4254.7 | 4254.8 | 96.3 |
| 10 | 4268.7 | 4268.9 | 95.6 |
| 11 | 4226.7 | 4227.0 | 95.2 |
| 12 | 4270.7 | 4270.9 | 99.9 |
| 13 | 4227.7 | 4227.4 | 99.9 |
| 14 | 4240.7 | 4241.0 | 99.9 |
| 15 | 4270.7 | 4270.6 | 99.9 |
| 16 | 4250.7 | 4250.9 | 99.9 |
| 17 | 4226.7 | 4226.9 | 99.9 |
| 18 | 4270.7 | 4270.8 | 99.9 |
| 19 | 4270.7 | 4270.5 | 99.9 |
| 20 | 4212.7 | 4212.7 | 99.9 |
| 21 | 4226.7 | 4226.8 | 99.9 |
| 22 | 4227.7 | 4227.8 | 99.9 |
| 23 | 4284.8 | 4284.7 | 99.9 |
| 24 | 4166.6 | 4166.9 | 99.9 |
| 25 | 4166.6 | 4166.6 | 99.9 |
| 26 | 4164.7 | 4164.7 | 98.1 |
| 27 | 4150.7 | 4150.4 | 99.9 |
| 28 | 4136.6 | 4136.5 | 99.9 |
| 29 | 4180.6 | 4181.0 | 99.9 |
| 30 | 4122.6 | 4122.6 | 99.9 |
| 31 | 4196.7 | 4197.0 | 98.9 |
| 32 | 4182.7 | 4182.7 | 99.9 |
| 33 | 4180.7 | 4180.9 | 99.9 |
| 34 | 4180.6 | 4180.5 | 99.9 |
| 35 | 4206.6 | 4206.8 | 99.9 |
| 36 | 4216.6 | 4217.0 | 99.9 |
| 37 | 4230.6 | 4231.1 | 99.9 |
| 38 | 4168.6 | 4168.2 | 99.9 |
| 39 | 4138.6 | 4139.1 | 99.9 |
| 40 | 4254.7 | 4255.4 | 97.7 |
| 41 | 4254.7 | 4255.9 | 98.2 |
| 42 | 4238.7 | 4238.5 | 99.9 |
| 43 | 4254.7 | 4254.7 | 96.5 |
| 44 | 4302.8 | 4302.7 | 98.8 |
| 45 | 4482.1 | 4482.4 | >99 |

In Vitro Radioligand NPY-Y1 and NPY-Y2 Receptor Binding Assays

Human neuroblastoma cell lines, SK-N-MC and SK-N-BE2 (American Type Culture Collection, Rockville, Md., USA), expressing the NPY-Y1 and NPY-Y2 receptors, respectfully, were cultured in EMEM containing 10% fetal calf serum and 5% chicken embryo extract, and maintained at 37° C. in a humidifed atmosphere of and 95% air and 5% $CO_2$.

For the in vitro NPY-Y1 and NPY-Y2 radioligand binding assays, the appropriate cells (SK-N-MC for NPY-Y1; SK-N-BE2 for NPY-Y2) were harvested, homogenized in 20 ml of ice-cold 50 mM Tris-HCl with a Brinkman Polytron (Westbury, N.Y., USA) (setting 6, 15 sec). The homogenates were washed twice by centrifugation (39,000 g/10 min), and the final pellets were resuspended in 50 mM Tris-HCl, containing 2.5 mM $MgCl_2$, 0.1 mg/ml bacitracin (Sigma Chemical, St. Louis, Mo., USA), and 0.1% BSA.

For assay, aliquots (0.4 ml) of the foregoing suspensions were incubated with 0.05 nM [$^{125}$I]PYY (2200 Ci/mmol, Perkin-Elmer, Boston, Mass.), with and without 0.05 ml of unlabeled competing test peptides. After a 100 min incubation (25° C.), the bound [$^{125}$I]PYY was separated from the free by rapid filtration through GF/C filters (Brandel, Gaithersburg, Md., USA), which had been previously soaked in 0.3% polyethyleneimine. The filters were then washed three times with 5-ml aliquots of ice-cold 50 mM Tris-HCl, and the bound radioactivity trapped on the filters was counted by gamma spectrometry (Wallac LKB, Gaithersburg, Md., USA). Specific binding was defined as the total [$^{125}$I]PYY bound minus that bound in the presence of 1000 nM PYY (Bachem, Torrence, Calif., USA). Inhibition constants (Ki) were calculated using the well-known Cheng-Prusoff equation, and said data, together with selectivity of said compounds with respect to the NPY-Y1 and the NPY-Y2, are given in Table 2.

Each of the compounds of Examples 1-38 and 40-45 was subjected to the immediately foregoing radioligand assays, and nearly all of said compounds were found to have Ki of under 100 nM, as well as some of the exemplified compounds having Ki values in sub-nM range. It was also found that nearly all of said compounds highly selectively bind to the NPY-Y1 compared to the NPY-Y2.

TABLE 2

| Example No. | Ki (nM) for Y1 | Ki (nM) for Y2 | Selectivity |
| --- | --- | --- | --- |
| 1 | 0.04 | 198 | Y1 |
| 2 | 0.08 | >1000 | Y1 |
| 3 | 0.11 | 944 | Y1 |
| 4 | 0.21 | 658 | Y1 |
| 5 | 0.68 | 420 | Y1 |
| 6 | 0.31 | 319 | Y1 |
| 7 | 0.60 | 347 | Y1 |
| 8 | 3.48 | 52 | Y1 |
| 9 | 2.58 | 420 | Y1 |
| 10 | 0.98 | 578 | Y1 |
| 11 | 2.95 | 178 | Y1 |
| 12 | 1.19 | 505 | Y1 |
| 13 | 3.47 | 727 | Y1 |
| 14 | 257.27 | >1000 | Y1 |
| 15 | 0.26 | 710 | Y1 |
| 16 | 0.29 | >1000 | Y1 |
| 17 | 0.03 | 595 | Y1 |
| 18 | 0.21 | 171 | Y1 |
| 19 | 0.24 | 997 | Y1 |
| 20 | 0.20 | >1000 | Y1 |
| 21 | 0.13 | 45 | Y1 |
| 22 | 1.23 | >1000 | Y1 |
| 23 | 0.20 | >1000 | Y1 |
| 24 | 0.19 | >1000 | Y1 |
| 25 | 0.85 | 841 | Y1 |
| 26 | 0.94 | 198 | Y1 |
| 27 | 0.74 | 104 | Y1 |
| 28 | 0.18 | 441 | Y1 |

TABLE 2-continued

| Example No. | Ki (nM) for Y1 | Ki (nM) for Y2 | Selectivity |
|---|---|---|---|
| 29 | 1.16 | >1000 | Y1 |
| 30 | 0.59 | 766 | Y1 |
| 31 | 1.91 | 202 | Y1 |
| 32 | 1.40 | 483 | Y1 |
| 33 | 239.06 | >1000 | Y1 |
| 34 | 69.78 | >1000 | Y1 |
| 35 | 3.58 | >1000 | Y1 |
| 36 | 34.23 | >1000 | Y1 |
| 37 | 52.94 | >1000 | Y1 |
| 38 | 502.28 | >1000 | Y1 |
| 39 | N/A | N/A | N/A |
| 40 | 11.80 | 895 | Y1 |
| 41 | 9.68 | >1000 | Y1 |
| 42 | 0.48 | 466 | Y1 |
| 43 | 0.67 | 22 | Y1 |
| 44 | 1.44 | 151 | Y1 |
| 45 | 55.85 | 38 | Y2 |

Administration

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids). A typical method of making a salt of a peptide of the present invention is well known in the art and can be accomplished by standard methods of salt exchange. Accordingly, the TFA salt of a peptide of the present invention (the TFA salt results from the purification of the peptide by using preparative HPLC eluting with TFA containing buffer solutions) can be converted into another salt, such as an acetate salt, by dissolving the peptide in a small amount of 0.25 N acetic acid aqueous solution. The resulting solution is applied to a semi-prep HPLC column (Zorbax, 300 SB, C-8). The column is eluted with (1) 0.1N ammonium acetate aqueous solution for 0.5 hours, (2) 0.25N acetic acid aqueous solution for 0.5 hours, and (3) a linear gradient (20% to 100% of solution B over 30 min) at a flow rate of 4 ml/min (solution A is 0.25N acetic acid aqueous solution; solution B is 0.25N acetic acid in acetonitrile/water, 80:20). The fractions containing the peptide are collected and lyophilized to dryness.

The dosage of active ingredient in the compositions of this invention may be varied, however, it is necessary that the amount of the active ingredient be such that a suitable dosage form is obtained. The selected dosage depends upon the desired therapeutic effect, the route of administration, and the duration of the treatment. In general, an effective dosage for the activities of this invention is in the range of $1 \times 10^{-7}$ to 200 mg/kg/day, preferably $1 \times 10^{-4}$ to 100 mg/kg/day, which can be administered as a single dose or divided into multiple doses.

The compounds of this invention can be administered by oral, parenteral (e.g., intramuscular, intraperitoneal, intravenous or subcutaneous injection, or implant), nasal, vaginal, rectal, sublingual, or topical routes of administration, and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include, without limitation, pharmaceutically acceptable emulsions, solutions, suspensions, syrups, elixirs, and the like, containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include, without limitation, sterile aqueous or non-aqueous solutions, suspensions, emulsions, and the like. Examples of non-aqueous solvents or vehicles include propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtering through a bacteria-retaining filter, incorporating sterilizing agents, irradiating, or heating the compositions. They can also be manufactured in the form of sterile solid compositions which can be dissolved in sterile water, or some other sterile injectable medium, immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents and patent applications. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. Pat. No. 5,821,221 teaches polymeric sustained release compositions comprising a bioactive agent and chitosan. U.S. Pat. No. 5,916,883 teaches sustained release compositions comprising a bioactive agent and cyclodextrin. PCT publication WO99/38536 teaches absorbable sustained release compositions of a bioactive agent. PCT publication WO00/04916 teaches a process for making microparticles comprising a therapeutic agent such as a peptide in an oil-in-water process. PCT publication WO00/09166 teaches complexes comprising a therapeutic agent such as a peptide and a phosphorylated polymer. PCT publication WO00/25826 teaches complexes comprising a therapeutic agent such as a peptide and a polymer bearing a non-polymerizable lactone.

Unless defined otherwise, all technical and scientific terms used herein have the same meaning as commonly understood by one of ordinary skill in the art to which this invention belongs. Also, all publications, patent applications, patents and other references mentioned herein are hereby incorporated by reference, each in its entirety.

What is claimed is:

1. A compound according to formula (I) (SEQ ID NO:2):

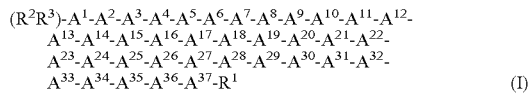

wherein:

$A^1$ is Tyr, $(X^1, X^2, X^3, X^4, X^5)$Phe, or HN—CH$((CH_2)_n$—N$(R^4R^5))$—C(O);

$A^2$ is Pro, 3Hyp, cis-3Hyp, 4Hyp, or cis-4Hyp;

$A^3$ is Ser, Abu, Aib, Ala, Thr, or HN—CH$((CH_2)_n$—N$(R^4R^5))$—C(O);

$A^4$ is Lys, Arg, hArg, Dab, Dap, Orn, or HN—CH$((CH_2)_n$—N$(R^4R^5))$—C(O);

$A^5$ is Pro, 3Hyp, cis-3Hyp, 4Hyp, or cis-4Hyp;

$A^6$ is Asp, Aib, Asn, Gln, Glu, or HN—CH$((CH_2)_n$—N$(R^4R^5))$—C(O);

$A^7$ is Asn, Aib, Gln, or HN—CH$((CH_2)_n$—N$(R^4R^5))$—C(O);

$A^8$ is Pro, 3Hyp, cis-3Hyp, 4Hyp, or cis-4Hyp;

$A^9$ is Gly, Aib, or HN—CH$((CH_2)_n$—N$(R^4R^5))$—C(O);

$A^{10}$ is Glu, Aib, Asn, Asp, Gln, or HN—CH$((CH_2)_n$—N$(R^4R^5))$—C(O);

$A^{11}$ is Asp, Aib, Asn, Gln, Glu, or HN—CH$((CH_2)_n$—N$(R^4R^5))$—C(O);

$A^{12}$ is Ala, Abu, Aib, Nva, Val, or HN—CH$((CH_2)_n$—N$(R^4R^5))$—C(O);

$A^{13}$ is Pro, 3Hyp, cis-3Hyp, 4Hyp, or cis-4Hyp;

$A^{14}$ is Ala, Abu, Aib, Nva, Val, or HN—CH$((CH_2)_n$—N$(R^4R^5))$—C(O);

$A^{15}$ is Glu, Aib, Asn, Asp, Gln, or HN—CH$((CH_2)_n$—N$(R^4R^5))$—C(O);

$A^{16}$ is Asp, Aib, Asn, Gln, Glu, or HN—CH$((CH_2)_n$—N$(R^4R^5))$—C(O);

$A^{17}$ is Met, Acc, Aib, Cha, Ile, Leu, hLeu, Nle, Nva, Tle, Val, or HN—CH$((CH_2)_n$—N$(R^4R^5))$—C(O);

$A^{18}$ is Ala, Abu, Aib, Nva, Val, or HN—CH$((CH_2)_n$—N$(R^4R^5))$—C(O);

$A^{19}$ is Arg, hArg, Apc, Dab, Dap, Lys, Orn, or HN—CH$((CH_2)_n$—N$(R^4R^5))$—C(O);

$A^{20}$ is Tyr, $(X^1, X^2, X^3, X^4, X^5)$Phe, or HN—CH$((CH_2)_n$—N$(R^4R^5))$—C(O);

$A^{21}$ is Tyr, $(X^1, X^2, X^3, X^4, X^5)$Phe, or HN—CH$((CH_2)_n$—N$(R^4R^5))$—C(O);

$A^{22}$ is Ser, Abu, Aib, Ala, Thr, or HN—CH$((CH_2)_n$—N$(R^4R^5))$—C(O);

$A^{23}$ is Ala, Abu, Aib, Nva, Val, or HN—CH$((CH_2)_n$—N$(R^4R^5))$—C(O);

$A^{24}$ is Leu, Acc, Cha, Ile, hLeu, Nle, Nva, Tle, Val, or HN—CH$((CH_2)_n$—N$(R^4R^5))$—C(O);

$A^{25}$ is Arg, hArg, Dab, Dap, Lys, Orn, or HN—CH$((CH_2)_n$—N$(R^4R^5))$—C(O);

$A^{26}$ is His, 2Pal, 3Pal, 4Pal, or HN—CH$((CH_2)_n$—N$(R^4R^5))$—C(O);

$A^{27}$ is Tyr, $(X^1, X^2, X^3, X^4, X^5)$Phe, or HN—CH$((CH_2)_n$—N$(R^4R^5))$—C(O);

$A^{28}$ is Ile, Acc, Cha, Leu, hLeu, Nle, Nva, Tle, Val, or HN—CH$((CH_2)_n$—N$(R^4R^5))$—C(O);

$A^{29}$ is Asn, Aib, Gln, or HN—CH$((CH_2)_n$—N$(R^4R^5))$—C(O);

$A^{30}$ is Leu, Acc, Cha, Ile, hLeu, Nle, Nva, Tle, Val, or HN—CH$((CH_2)_n$—N$(R^4R^5))$—C(O);

$A^{31}$ is Ile, Acc, Cha, Leu, hLeu, Nle, Nva, Tle, Val, or HN—CH$((CH_2)_n$—N$(R^4R^5))$—C(O);

$A^{32}$ is Thr, Aib, Ser, or HN—CH$((CH_2)_n$—N$(R^4R^5))$—C(O);

$A^{33}$ is Arg, hArg, Dab, Dap, Lys, Orn, or HN—CH$((CH_2)_n$—N$(R^4R^5))$—C(O);

A³⁴ is Dhp, 4Hyp, Inp, Nip, Tic, or HN—CH((CH₂)ₙ—N(R⁴R⁵))—C(O);

A³⁵ is Arg, Aic, Apc, hArg, Dab, Dap, Lys, Orn, NH₂Phe, NH₂CH₂Phe, or HN—CH((CH₂)ₙ—N(R⁴R⁵))—C(O);

A³⁶ is Tyr, Aic, (X¹, X², X³, X⁴, X⁵)Phe, or HN—CH((CH₂)ₙ—N(R⁴R⁵))—C(O);

A³⁷ is HN—CH((CH₂)ₙ—N(R⁴R⁵))—C(O) or deleted;

R¹ is OH, NH₂, (C₁₋₃₀)alkoxy, or NH—X⁶—CH₂—X⁷, wherein X⁶ is a (C₁₋₄₀)alkyl or (C₂₋₄₀) alkenyl, and wherein X⁷ is H, OH, CO₂H, or C(O)—NH₂;

R² and R³ each is, independently for each occurrence, selected from the group consisting of H, (C₁₋₃₀)alkyl, (C₁₋₃₀)heteroalkyl, (C₁₋₃₀)acyl, (C₂₋₃₀)alkenyl, (C₂₋₃₀) alkynyl, aryl(C₁₋₃₀)alkyl, aryl(C₁₋₃₀)acyl, substituted (C₁₋₃₀)alkyl, substituted (C₁₋₃₀)heteroalkyl, substituted (C₂₋₃₀)acyl, substituted (C₂₋₃₀)alkenyl, substituted (C₂₋₃₀)alkynyl, substituted aryl(C₁₋₃₀)alkyl, and substituted aryl(C₁₋₃₀)acyl;

provided that when R² is (C₁₋₃₀)acyl, aryl(C₁₋₃₀)acyl, substituted (C₂₋₃₀)acyl, or substituted aryl(C₁₋₃₀)acyl, R³ is H, (C₁₋₃₀)alkyl, (C₁₋₃₀)heteroalkyl, (C₂₋₃₀)alkenyl, (C₂₋₃₀) alkynyl, aryl(C₁₋₃₀)alkyl, substituted (C₁₋₃₀)alkyl, substituted (C₁₋₃₀)heteroalkyl, substituted (C₂₋₃₀)alkenyl, substituted (C₂₋₃₀)alkynyl, or substituted aryl(C₁₋₃₀)alkyl;

R⁴ and R⁵ each is, independently for each occurrence, H, (C₁₋₄₀)alkyl, (C₁₋₄₀) heteroalkyl, (C₁₋₄₀)acyl, (C₂₋₄₀) alkenyl, (C₂₋₄₀)alkynyl, aryl(C₁₋₄₀)alkyl, aryl(C₁₋₄₀) acyl, substituted (C₁₋₄₀)alkyl, substituted (C₁₋₄₀)heteroalkyl, substituted (C₁₋₄₀)acyl, substituted (C₂₋₄₀) alkenyl, substituted (C₂₋₄₀)alkynyl, substituted aryl(C₁₋₄₀)alkyl, substituted aryl(C₁₋₄₀) acyl, (C₁₋₄₀) alkylsulfonyl, or C(NH)—NH₂, wherein when R⁴ is (C₁₋₄₀)acyl, aryl(C₁₋₄₀)acyl, substituted (C₁₋₄₀)acyl, substituted aryl(C₁₋₄₀)acyl, (C₁₋₄₀)alkylsulfonyl, or C(NH)—NH₂, then R⁵ is H or (C₁-C₄₀)alkyl, (C₁₋₄₀) heteroalkyl, (C₂₋₄₀)alkenyl, (C₂₋₄₀)alkynyl, aryl(C₁₋₄₀) alkyl, substituted (C₁₋₄₀)alkyl, substituted (C₁₋₄₀)heteroalkyl, substituted (C₂₋₄₀)alkenyl, substituted (C₂₋₄₀) alkynyl, or substituted aryl(C₁₋₄₀)alkyl;

n is, independently for each occurrence, 1, 2, 3, 4, or 5;

X¹, X², X³, X⁴, and X⁵ each is, independently for each occurrence, H, F, Cl, Br, I, (C₁₋₁₀)alkyl, substituted (C₁₋₁₀)alkyl, aryl, substituted aryl, OH, CH₂NH₂, NH₂, NO₂, or CN; and provided that the compound contains at least one substitution with an unnatural amino acid;

or a pharmaceutically acceptable salt thereof.

2. The compound according to claim 1, wherein:

A¹ is Tyr;
A² is Pro;
A³ is Ser or Aib;
A⁴ is Lys;
A⁵ is Pro;
A⁶ is Asp or Aib;
A⁷ is Asn or Aib;
A⁸ is Pro;
A⁹ is Gly or Aib;
A¹⁰ is Glu or Aib;
A¹¹ is Asp or Aib;
A¹² is Ala or Aib;
A¹³ is Pro;
A¹⁴ is Ala or Aib;
A¹⁵ is Glu or Aib;
A¹⁶ is Asp or Aib;
A¹⁷ is Met, A6c, Aib, or Nle;
A¹⁸ is Ala or Aib;
A¹⁹ is Arg;
A²⁰ is Tyr;
A²¹ Tyr;
A²² is Ser or Aib;
A²³ is Ala or Aib;
A²⁴ is Leu or A6c;
A²⁵ is Arg;
A²⁶ is His;
A²⁷ is Tyr;
A²⁸ is Ile or A6c;
A²⁹ is Asn or Aib;
A³⁰ is Leu or A6c;
A³¹ is Ile, A6c, or Leu;
A³² is Thr or Aib;
A³³ is Arg;
A³⁵ is Arg, Apc, Lys, 4NH₂Phe, or 4NH₂CH₂Phe;
A³⁶ is Tyr or Aic;
A³⁷ is deleted;
R¹ is NH₂;
R² and R³ each is, independently for each occurrence, H or (C₁₋₃₀)acyl;
provided that when R² is (C₁₋₃₀)acyl, R³ is H;
R⁴ and R⁵ each is, independently for each occurrence, H or (C₁₋₄₀)acyl;
n is 4; and
X¹, X², X³, X⁴, and X⁵ each is, independently for each occurrence, H, CH₂NH₂, or NH₂;
or a pharmaceutically acceptable salt thereof.

3. The compound according to claim 1, wherein HN—CH((CH2)n—N(R⁴R⁵))—C(O) is Lys(Nᵋ—C(O)—(CH2)12—CH3), or a pharmaceutically acceptable salt thereof.

4. The compound according to claim 1, wherein said compound is:

[Aib¹⁰, 4Hyp³⁴]hNPY(1-36)-NH₂;  (SEQ ID NO: 3)

[Aib¹⁷, 4Hyp³⁴]hNPY(1-36)-NH₂;  (SEQ ID NO: 4)

[Aib¹¹,¹⁷, 4Hyp³⁴]hNPY(1-36)-NH₂;  (SEQ ID NO: 5)

[4Hyp³⁴]hNPY(1-36)-NH₂;  (SEQ ID NO: 6)

[Aib²², 4Hyp³⁴]hNPY(1-36)-NH₂;  (SEQ ID NO: 7)

[A6c³¹, 4Hyp³⁴]hNPY(1-36)-NH₂;  (SEQ ID NO: 8)

[A6c³⁰, 4Hyp³⁴]hNPY(1-36)-NH₂;  (SEQ ID NO: 9)

[A6c²⁸, 4Hyp³⁴]hNPY(1-36)-NH₂;  (SEQ ID NO: 10)

[Aib³, 4Hyp³⁴]hNPY(1-36)-NH₂;  (SEQ ID NO: 11)

[A6c²⁴, 4Hyp³⁴]hNPY(1-36)-NH₂;  (SEQ ID NO: 12)

[Aib⁶, 4Hyp³⁴]hNPY(1-36)-NH₂;  (SEQ ID NO: 13)

[Aib¹⁸, 4Hyp³⁴]hNPY(1-36)-NH₂;  (SEQ ID NO: 14)

[Aib²⁹, 4Hyp³⁴]hNPY(1-36)-NH₂;  (SEQ ID NO: 15)

[Aib³², 4Hyp³⁴]hNPY(1-36)-NH₂; (SEQ ID NO: 16)

[Aib²³, 4Hyp³⁴]hNPY(1-36)-NH₂; (SEQ ID NO: 17)

[A6c¹⁷, 4Hyp³⁴]hNPY(1-36)-NH₂; (SEQ ID NO: 18)

[Aib¹¹, 4Hyp³⁴]hNPY(1-36)-NH₂; (SEQ ID NO: 19)

[Aib¹², 4Hyp³⁴]hNPY(1-36)-NH₂; (SEQ ID NO: 20)

[Aib¹⁴, 4Hyp³⁴]hNPY(1-36)-NH₂; (SEQ ID NO: 21)

[Aib¹⁵, 4Hyp³⁴]hNPY(1-36)-NH₂; (SEQ ID NO: 22)

[Aib¹⁶, 4Hyp³⁴]hNPY(1-36)-NH₂; (SEQ ID NO: 23)

[Aib⁷, 4Hyp³⁴]hNPY(1-36)-NH₂; (SEQ ID NO: 24)

[Aib⁹, 4Hyp³⁴]hNPY(1-36)-NH₂; (SEQ ID NO: 25)

[Aib¹⁰,¹⁷, 4Hyp³⁴]hNPY(1-36)-NH₂; (SEQ ID NO: 26)

[Aib¹⁵,¹⁷, 4Hyp³⁴]hNPY(1-36)-NH₂; (SEQ ID NO: 27)

[Aib¹¹,¹⁵, Nle¹⁷, 4Hyp³⁴]hNPY(1-36)-NH₂; (SEQ ID NO: 28)

[Aib¹⁰,¹⁵, Nle¹⁷, 4Hyp³⁴]hNPY(1-36)-NH₂; (SEQ ID NO: 29)

[Aib¹¹,¹⁵,¹⁷, 4Hyp³⁴]hNPY(1-36)-NH₂; (SEQ ID NO: 30)

[Aib¹²,¹⁵,¹⁷, 4Hyp³⁴]hNPY(1-36)-NH₂; (SEQ ID NO: 31)

[Aib¹⁰,¹⁵,¹⁷, 4Hyp³⁴]hNPY(1-36)-NH₂; (SEQ ID NO: 32)

[Aib¹¹,¹⁶, 4Hyp³⁴]hNPY(1-36)-NH₂; (SEQ ID NO: 33)

[Aib¹⁰,¹⁶, 4Hyp³⁴]hNPY(1-36)-NH₂; (SEQ ID NO: 34)

[Aib¹⁷, 4Hyp³⁴, Apc³⁵]hNPY(1-36)-NH₂; (SEQ ID NO: 36)

[Aib¹⁷, 4Hyp³⁴, Aic³⁶]hNPY(1-36)-NH₂; (SEQ ID NO: 37)

[Aib¹⁷, 4Hyp³⁴, 4NH₂Phe³⁵]hNPY(1-36)-NH₂; (SEQ ID NO: 38)

[Aib¹⁷, 4Hyp³⁴, 4NH₂CH₂Phe³⁵]hNPY(1-36)-NH₂; (SEQ ID NO: 39)

[Nip³⁴]hNPY(1-36)-NH₂; (SEQ ID NO: 42)

[Inp³⁴]hNPY(1-36)-NH₂; (SEQ ID NO: 43)

[Dhp³⁴]hNPY(1-36)-NH₂; (SEQ ID NO: 44)

[Tic³⁴]hNPY(1-36)-NH₂; (SEQ ID NO: 46)
or

[Leu³¹, Lys³⁴(Nᵉ—C(O)—(CH₂)₁₂—CH₃)]hNPY(1-36)-NH₂; (SEQ ID NO: 47)

or a pharmaceutically acceptable salt thereof.

5. The compound according to claim 1, wherein $A^{34}$ is 4Hyp, or a pharmaceutically acceptable salt thereof.

6. The compound according to claim 5, wherein said compound is:

[Aib¹⁰, 4Hyp³⁴]hNPY(1-36)-NH₂; (SEQ ID NO: 3)

[Aib¹⁷, 4Hyp³⁴]hNPY(1-36)-NH₂; (SEQ ID NO: 4)

[Aib¹¹,¹⁷, 4Hyp³⁴]hNPY(1-36)-NH₂; (SEQ ID NO: 5)

[4Hyp³⁴]hNPY(1-36)-NH₂; (SEQ ID NO: 6)

[Aib²², 4Hyp³⁴]hNPY(1-36)-NH₂; (SEQ ID NO: 7)

[A6c³¹, 4Hyp³⁴]hNPY(1-36)-NH₂; (SEQ ID NO: 8)

[A6c³⁰, 4Hyp³⁴]hNPY(1-36)-NH₂; (SEQ ID NO: 9)

[A6c²⁸, 4Hyp³⁴]hNPY(1-36)-NH₂; (SEQ ID NO: 10)

[Aib₃, 4Hyp³⁴]hNPY(1-36)-NH₂; (SEQ ID NO: 11)

[A6c²⁴, 4Hyp³⁴]hNPY(1-36)-NH₂; (SEQ ID NO: 12)

[Aib⁶, 4Hyp³⁴]hNPY(1-36)-NH₂; (SEQ ID NO: 13)

[Aib¹⁸, 4Hyp³⁴]hNPY(1-36)-NH₂; (SEQ ID NO: 14)

[Aib²⁹, 4Hyp³⁴]hNPY(1-36)-NH₂; (SEQ ID NO: 15)

[Aib³², 4Hyp³⁴]hNPY(1-36)-NH₂; (SEQ ID NO: 16)

[Aib²³, 4Hyp³⁴]hNPY(1-36)-NH₂; (SEQ ID NO: 17)

[A6c¹⁷, 4Hyp³⁴]hNPY(1-36)-NH₂; (SEQ ID NO: 18)

[Aib¹¹, 4Hyp³⁴]hNPY(1-36)-NH₂; (SEQ ID NO: 19)

[Aib¹², 4Hyp³⁴]hNPY(1-36)-NH₂; (SEQ ID NO: 20)

[Aib¹⁴, 4Hyp³⁴]hNPY(1-36)-NH₂; (SEQ ID NO: 21)

[Aib¹⁵, 4Hyp³⁴]hNPY(1-36)-NH₂; (SEQ ID NO: 22)

[Aib¹⁶, 4Hyp³⁴]hNPY(1-36)-NH₂; (SEQ ID NO: 23)

```
[Aib⁷, 4Hyp³⁴]hNPY(1-36)-NH₂;                    (SEQ ID NO: 24)

[Aib⁹, 4Hyp³⁴]hNPY(1-36)-NH₂;                    (SEQ ID NO: 25)

[Aib¹⁰,¹⁷, 4Hyp³⁴]hNPY(1-36)-NH₂;                (SEQ ID NO: 26)

[Aib¹⁵,¹⁷, 4Hyp³⁴]hNPY(1-36)-NH₂;                (SEQ ID NO: 27)

[Aib¹¹,¹⁵, Nle¹⁷, 4Hyp³⁴]hNPY(1-36)-NH₂;         (SEQ ID NO: 28)

[Aib¹⁰,¹⁵, Nle¹⁷, 4Hyp³⁴]hNPY(1-36)-NH₂;         (SEQ ID NO: 29)

[Aib¹¹,¹⁵,¹⁷, 4Hyp³⁴]hNPY(1-36)-NH₂;             (SEQ ID NO: 30)

[Aib¹²,¹⁵,¹⁷, 4Hyp³⁴]hNPY(1-36)-NH₂;             (SEQ ID NO: 31)

[Aib¹⁰,¹⁵,¹⁷, 4Hyp³⁴]hNPY(1-36)-NH₂;             (SEQ ID NO: 32)

[Aib¹¹,¹⁶, 4Hyp³⁴]hNPY(1-36)-NH₂;                (SEQ ID NO: 33)

[Aib¹⁰,¹⁶, 4Hyp³⁴]hNPY(1-36)-NH₂;                (SEQ ID NO: 34)

[Aib¹⁷, 4Hyp³⁴, Apc³⁵]hNPY(1-36)-NH₂;            (SEQ ID NO: 36)

[Aib¹⁷, 4Hyp³⁴, Aic³⁶]hNPY(1-36)-NH₂;            (SEQ ID NO: 37)

[Aib¹⁷, 4Hyp³⁴, 4NH₂Phe³⁵]hNPY(1-36)-NH₂;        (SEQ ID NO: 38)
or

[Aib¹⁷, 4Hyp³⁴, 4NH₂CH₂Phe³⁵]hNPY(1-36)-NH₂;     (SEQ ID NO: 39)
``` or a pharmaceutically acceptable salt thereof.

7. The compound according to claim 1, wherein the peptide bond between $A^{35}$ and $A^{36}$ is replaced by a pseudopeptide bond, or a pharmaceutically acceptable salt thereof.

8. The compound according to claim 7, wherein $A^{35}$-$A^{36}$ is Lys-ψ(CH₂—NH)Tyr or Lys-ψ(CH₂—N(Ac))Tyr, or a pharmaceutically acceptable salt thereof.

9. The compound according to claim 8, wherein said compound is:

```
[Aib¹¹,¹⁷, 4Hyp³⁴, Lys³⁵-ψ(CH₂-N(Ac))Tyr³⁶]hNPY   (SEQ ID NO: 35)
(1-36)-NH₂;

[Aib¹⁷, 4Hyp³⁴, Lys³⁵-ψ(CH₂-NH)Tyr³⁶]hNPY(1-36)-NH₂;   (SEQ ID NO: 40)
or

[Aib¹¹,¹⁷, 4Hyp³⁴, Lys³⁵-ψ(CH₂-NH)Tyr³⁶]hNPY      (SEQ ID NO: 41)
(1-36)-NH₂;
``` or a pharmaceutically acceptable salt thereof.

10. The pharmaceutical composition comprising an effective amount of a compound according to claim 1 or a pharmaceutically acceptable salt thereof.

11. The pharmaceutical composition of claim 10, further comprising a pharmaceutically acceptable carrier.

12. A method for treating a disorder or a disease mediated by neuropeptide Y-receptor binding comprising administering to a subject in need thereof the therapeutically effective amount of the compound according to claim 1.

13. The method according to claim 12, wherein said neuropeptide Y receptor is a NPY-Y1 receptor.

14. The method according to claim 12, wherein said disorder or disease pertains to the heart, blood vessels, renal system, vasospasm, heart failure, shock, cardiac hypertrophy, increased blood pressure, angina, myocardial infarction, sudden cardiac death, arrhythmia, peripheral vascular disease, impaired flow of fluid, abnormal mass transport, or renal failure.

15. The method according to claim 12, wherein said disorder or disease is related to the central nervous system, cerebral infarction, neurodegeneration, epilepsy, stroke, cerebral vasospasm, cerebral hemorrhage, depression, anxiety, schizophrenia, or dementia.

16. The method according to claim 12, wherein said disorder or disease is related to abnormal gastrointestinal motility and secretion, different forms of ileus, urinary incontinence, or Crohn's disease.

17. The method according to claim 12, wherein said disorder or disease pertains to abnormal drink and food intake disorders, anorexia or metabolic disorders.

18. The method according to claim 12, wherein said disorder or disease is a respiratory disease, asthma or bronchoconstriction.

19. The method according to claim 12, wherein said disorder or disease is related to abnormal release of leutinizing hormone, growth hormone, insulin, or prolactin.

20. The method according to claim 13, wherein said condition or disease is a tumor expressing the NPY-Y1 receptor.

21. The method of claim 20, wherein said tumor is breast cancer, ovarian cancer, or glioblastoma.

22. The method according to claim 13, wherein said condition or disease mediated by the NPY-Y1 receptor binding is hypertension.

23. The method according to claim 12, wherein said condition or disease is obesity, hyperphasia, or bulimia.

* * * * *

UNITED STATES PATENT AND TRADEMARK OFFICE
CERTIFICATE OF CORRECTION

PATENT NO. : 8,440,611 B2  
APPLICATION NO. : 13/202030  
DATED : May 14, 2013  
INVENTOR(S) : Zheng Xin Dong, Kevin Zhou and Daniel B. DeOliveira Page 1 of 1

It is certified that error appears in the above-identified patent and that said Letters Patent is hereby corrected as shown below:

In the claims

Claim 4, Column 78, Line 40, " [Aib$^{17}$, 4Hyp3$^{34}$]hNPY(1-36)-NH$_2$;" should read -- [Aib$^{17}$, 4Hyp$^{34}$]hNPY(1-36)-NH$_2$; --

Claim 4, Column 78, Line 66, " [Aib$^{29}$, 4Hyp3$^{34}$]hNPY(1-36)-NH$_2$;" should read -- [Aib$^{29}$, 4Hyp$^{34}$]hNPY(1-36)-NH$_2$; --

Claim 12, Column 82, Line 15, "by neuropeptide Y-receptor binding comprising administer-" should read -- by neuropeptide Y-receptor binding, comprising administer- --

Signed and Sealed this  
Thirtieth Day of July, 2013

Teresa Stanek Rea  
*Acting Director of the United States Patent and Trademark Office*